United States Patent [19]

Sterk

[11] Patent Number: 6,103,718

[45] Date of Patent: Aug. 15, 2000

[54] PHTHALAZINONES

[75] Inventor: Geert Jan Sterk, Utrecht, Netherlands

[73] Assignee: Byk Gulden Lomberg Chemische Fabrik GmbH, Constance, Germany

[21] Appl. No.: 09/341,135

[22] PCT Filed: Jan. 12, 1998

[86] PCT No.: PCT/EP98/00124

§ 371 Date: Jul. 14, 1999

§ 102(e) Date: Jul. 14, 1999

[87] PCT Pub. No.: WO98/31674

PCT Pub. Date: Jul. 23, 1998

[30] Foreign Application Priority Data

Jan. 15, 1997 [EP] European Pat. Off. .............. 97100488

[51] Int. Cl.$^7$ ...................... C07D 237/32; C07D 401/06; C07D 413/06; A61K 31/502

[52] U.S. Cl. ........................ 514/234.3; 544/237; 544/116; 514/248

[58] Field of Search ..................................... 544/237, 116; 514/248, 234.3

[56] References Cited

U.S. PATENT DOCUMENTS 4,289,774  9/1981  Schacht et al. .
5,849,741  12/1998  Watanable et al. .

FOREIGN PATENT DOCUMENTS

WO 94/12461  6/1994  European Pat. Off. .
634404  1/1995  European Pat. Off. .

*Primary Examiner*—Mukund J. Shah
*Assistant Examiner*—Beth Jayaram
*Attorney, Agent, or Firm*—Jacobson, Price, Holman & Stern, PLLC

[57] ABSTRACT

Compounds of formula I

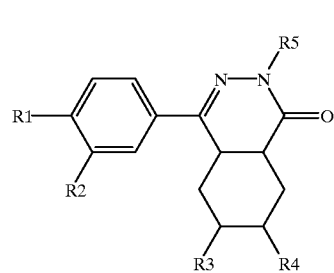

(I)

wherein R1, R2, R3, R4 and R5 have the means set forth in the description are selective cyclic nucleotide phosphodiesterase (PDE) inhibitors (specifically of type 4), which are effective bronchial therapeutics.

11 Claims, No Drawings

PHTHALAZINONES

This application is a 371 of PCT/EP98/00124 filed Jan. 12, 1998.

FIELD OF APPLICATION OF THE INVENTION

The invention relates to novel Phthalazinones which are used in the pharmaceutical industry for the production of medicaments.

KNOWN TECHNICAL BACKGROUND

International Patent Application WO91/12251 describes phthalazinones having bronchodilating and thromboxane A2 synthetase inhibiting properties. International Patent Application WO94/12461 describes 3-aryl-pyridazin-6-one derivates as selective PDE4 inhibitors.

DESCRIPTION OF THE INVENTION

It has now been found that phthalazinones, which are described in greater details below, have surprising and particularly advantageous properties.

The invention thus relates to compounds of the formula I,

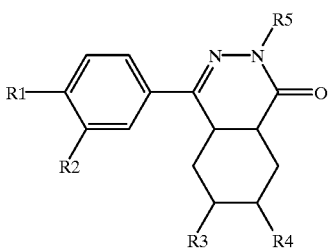

(I)

in which
R1 is 1–4C-alkoxy or 1–4C-alkoxy which is completely or predominantly substituted by fluorine,
R2 is 1–8C-alkoxy, 3–7C-cycloalkoxy, 3–7C-cycloalkylmethoxy or 1–4C-alkoxy which is completely or predominantly substituted by fluorine.
R3 and R4 are both hydrogen or together form an additional bond,
R5 is R6, —$C_mH_{2m}$—R7, —$C_nH_{2n}$—C(O)R8, —CH($R_b$)$_2$ or —$C_pH_{2p}$—Ar, in which
R6 is hydrogen (H), 1–8C-alkyl, 3–10C-cycloalkyl, 3–7C-cycloalkylmethyl, 3–7C-alkenyl, 3–7C-alkynyl, phenyl-3–4C-alkenyl, 7–10C-polycycloalkyl, naphthyl, pyridyl, pyrazinyl, pyridazinyl, primidyl, quinazolinyl, quinoxalinyl, cinnolinyl, isoquinolyl, quinolyl, indanyl, benzoxazolyl, benzothiazolyl, oxazolyl, thiazolyl, N-methylpiperidyl, tetrahydropyranyl, tetrahydrothiapyranyl, or an unsubstituted or by R61 and/or R62 substituted phenyl radical, in which
R61 is 1–4C-alkyl, 1–4C-alkoxy, nitro, halogen, carboxyl, carboxy-1–4C-alkyl, 1–4C-alkoxycarbonyl, hydroxy-1–4C-alkyl, amino, mono- or di-1–4-C-alkylamino, 1–4C-alkylcarbonylamino, aminocarbonyl, mono- or di-1–4C-alkylaminocarbonyl, aminosulfonyl, mono- or di-1–4C-alkylaminosulfonyl, 4-methylphenylsulfonamido, tetrazol-5-yl, 2-(1–4C-alkyl)tetrazol-5-yl or 2-benzyl-tetrazol-5-yl and
R62 is 1–4C-alkyl, 1–4C-alkoxy, nitro or halogen,
R7 is hydroxyl, halogen, cyano, nitro, nitroxy(—O—$NO_2$), carboxyl, carboxyphenyloxy, phenoxy, 1–4C-alkoxy, 3–7C-cycloalkoxy, 3–7C-cycloalkylmethoxy, 1–4C-alkylcarbonyl, 1–4C-alkylcarbonyloxy, 1–4C-alkylcarbonylamino, 1–4C-alkoxycarbonyl, aminocarbonyl, mono- or di-1–4C-alkylaminocarbonyl, amino, mono- or di-1–4C-alkylamino, or an unsubstituted or by R71 and/or R72 substituted piperidyl, piperazinyl, pyrrolidinyl or morpholinyl radical, where
R71 is hydroxyl, 1–4C-alkyl, hydroxy-1–4C-alkyl or 1–4C-alkoxycarbonyl, and
R72 is 1–4C-alkyl, carboxyl, aminocarbonyl or 1–4C-alkoxycarbonyl,
R8 is an unsubstituted or by R81 and/or R82 substituted phenyl, naphthyl, phenanthrenyl or anthracenyl radical, in which
R81 is hydroxyl, halogen, cyano, 1–4C-alkyl, 1–4C-alkoxy, carboxyl, aminocarbonyl, mono- or di-1–4C-alkylaminocarbonyl, 1–4C-alkylcarbonyloxy, 1–4C-alkoxycarbonyl, amino, mono- or di-1–4C-alkylamino, 1–4C-alkylcarbonylamino, or 1–4C-alkoxy which is completely or predominantly substituted by fluorine, and
R82 is hydroxyl, halogen, 1–4C-alkyl, 1–4C-alkoxy or 1–4C-alkoxy which is completely or predominantly substituted by fluorine,
R9 is —$C_qH_{2q}$—phenyl,
Ar is an unsubstituted phenyl, naphthyl, pyridyl, pyrazinyl, pyridazinyl, primidinyl, quinazolinyl, quinoxalinyl, cinnolinyl, isoquinolyl, quinolyl, benzimidazolyl, benzoxazolyl, benzothiazolyl, benzotriazolyl, N-benzosuccinimidyl, imidazolyl, pyrazolyl, oxazolyl, thiazolyl, furyl, thienyl, pyrrolyl, a 2-(1–4C-alkyl)-thiazol-4-yl radical, or a phenyl radical substituted by R10 and/or R11, in which
R10 is hydroxyl, halogen, nitro, 1–4C-alkyl, trifluoromethyl, 1–4C-alkoxy, carboxyl, carboxy-1–4C-alkyl, 1–4C-alkylcarbonyloxy, 1–4C-alkoxycarbonyl, amino, mono- or di-1–4C-alkyl-amino, 1–4C-alkylcarbonylamino, aminocarbonyl or mono- or di-1–4-C-alkylamino-carbonyl, and
R11 is hydroxyl, halogen, nitro, 1–4C-alkyl or 1–4C-alkoxy,
m is an integer from 1 to 8,
n is an integer from 1 to 4,
p is an integer from 1 to 6,
q is an integer from 0 to 2.
and the salts of these compounds.

On embodiment (embodiment a) of the invention are compounds of the formula I, in which
R1 is 1–4C-alkoxy or 1–4C-alkoxy which is completely or predominantly substituted by fluorine,
R2 is 1–8C-alkoxy, 3–7C-cycloalkoxy, 3–7C-cycloalkylmethoxy or 1–4C-alkoxy which is completely or predominantly substituted by fluorine,
R3 and R4 are both hydrogen or together form an additional bond,
R5 is R6, —$C_mH_{2m}$—R7, —$C_nH_{2n}$—C(O)R8, —CH(R9)$_2$ or —$C_pH_{2p}$—Ar, in which
R6 is hydrogen (H), 1–8C-alkyl, 3–10C-cycloalkyl, 3–7C-cycloalkylmethyl, 3–7C-alkenyl, 3–7C-alkynyl, phenyl-3–4C-alkenyl, bornyl, norbornyl, adamantyl or an unsubstituted or by R61 and/or R62 substituted phenyl radical, in which
R61 is 1–4C-alkyl, 1–4C-alkoxy, nitro or halogen, and
R62 is 1–4C-alkyl, nitro or halogen,
R7 is hydroxyl, halogen, cyano, nitro, carboxyl, phenoxy, 1–4C-alkoxy, 3–7C-cycloalkoxy, 3–7C-cycloalkylmethoxy, 1–4C-alkylcarbonyl, 1–4C-alkylcarbonyloxy, 1–4C-alkylcarbonylamino, 1–4C-alkoxycarbonyl, aminocarbonyl, mono- or di-1–4C-alkylaminocarbonyl, amino, mono- or di-1–4C- alkylamino, or an unsubstituted or by R71 and/or R72 substituted piperidyl, piperazinyl, pyrrolidinyl or morpholinyl radical, where R71 is hydroxyl, 1–4C-alkyl, 1–4C-hydroxyalkyl or 1–4C-alkoxycarbonyl, and R72 is 1–4C-alkyl, carboxyl, aminocarbonyl or 1–4C-alkoxycarbonyl, R8 is an unsubstituted or by R81 and/or R82 substituted phenyl, naphthyl, phenanthrenyl or anthracenyl radical, in which R81 is hydroxyl, halogen, cyano, 1–4C-alkyl, 1–4C-alkoxy, carboxyl, aminocarbonyl, mono- or di-1–4C-alkylaminocarbonyl, 1–4C-alkylcarbonyloxy, 1–4C-alkoxycarbonyl, amino, mono- or di-1–4C-alkylamino, 1–4C-alkylcarbonylamino, or 1–4C-alkoxy which is completely or predominantly substituted by fluorine, and R82 is hydroxyl, halogen, 1–4C-alkyl, 1–4C-alkoxy or 1–4C-alkoxy which is completely or predominantly substituted by fluorine, R9 is —$C_qH_{2q}$—phenyl, Ar is an unsubstituted phenyl, naphthyl, pyridyl, pyrazinyl, pyridazinyl, primidinyl, quinazolinyl, quinoxalinyl, cinnolinyl, isoquinolyl, quinolyl, benzimidazolyl, benzoxazolyl, benzothiazolyl, benzotriazolyl, imidazolyl, pyrazolyl, oxazolyl, thiazolyl, furyl, thienyl, pyrrolyl, a 2-(1–4C-alkyl)-thiazol-4-yl radical, or a phenyl radical substituted by R10 and/or R11, in which R10 is hydroxyl, halogen, nitro, 1–4C-alkyl, trifluoromethyl, 1–4C-alkoxy, carboxyl, carboxy-1–4C-alkyl, 1–4C-alkylcarbonyloxy, 1–4C-alkoxycarbonyl, amino, mono- or di-1–4C-alkylamino, 1–4C-alkylcarbonylamino, aminocarbonyl or mono- or di-1–4C-alkylaminocarbonyl, and R11 is hydroxyl, halogen, nitro, 1–4C-alkyl or 1–4C-alkoxy, m is an integer from 1 to 8, n is an integer from 1 to 4, p is an integer from 1 to 4, q is an integer from 0 to 2, and the salts of these compounds.

1–8C-Alkyl is a straight-chain or branched alkyl radical having 1 to 8 carbon atoms. Examples are the octyl, heptyl, isoheptyl (5-methylhexyl), hexyl, isohexyl (4-methylpentyl), neohexyl (3,3-dimethylbutyl), neopentyl (2,2-dimethylpropyl), pentyl, isopentyl (3-methylbutyl), 1-ethylpropyl, butyl, isobutyl, sec-butyl, tert-butyl, propyl, isopropyl, ethyl and methyl radicals.

1–4C-Alkyl is a straight-chain or branched alkyl radical having 1 to 4 carbon atoms. Examples are the butyl, isobutyl, sec-butyl, tert-butyl, propyl, isopropyl, ethyl and methyl radicals.

1–4C-Alkoxy is a radical, which, in addition to the oxygen atom contains a straight-chain or branched alkyl radical having 1 to 4 carbon atoms. Alkoxy radicals having 1 to 4 carbon atoms which may be mentioned in this context are, for example, the butoxy, iso-butoxy, sec-butoxy, tert-butoxy, propoxy, isopropoxy, ethoxy and methoxy radicals.

1–4C-Alkoxy which is completely or predominantly substituted by fluorine is, for example, the 2,2,3,3,3-pentafluoropropoxy, the perfluoroethoxy, the 1,2,2-trifluoroethoxy and in particular the 1,1,2,2-tetraflurorethoxy, the 2,2,2-trifluoroethoxy, the trifluoromethoxy and the difluoromethoxy radical.

1–8C- Alkoxy is radical which, in addition to the oxygen atom, contains a straight-chain or branched alkyl radical having 1 to 8 carbon atoms. Alkoxy radicals having 1 to 8 carbon atoms which may be mentioned in this context are, for example, the octyloxy, heptyloxy, isoheptyloxy (5-methylhexyloxy), hexyloxy, isohexyloxy (4-methylpentyloxy), neohexyloxy (3,3-dimethylbutoxy), pentyloxy, isopentyloxy (3-methylbutoxy), neopentyloxy (2,2-dimethylpropoxy), butoxy, isobutoxy, sec-butoxy, tert-butoxy, propoxy, isopropoxy, ethoxy and methoxy radicals.

3–7C-Cycloalkoxy stands for cyclopropyloxy, cyclobutyloxy, cyclopentyloxy, cyclohexyloxy or cycloheptyloxy, of which cyclopropyloxy, cyclobutyloxy and cyclopentyloxy are preferred.

3–7C-Cycloalkylmethoxy stands for cyclopropylmethoxy, cyclobutylmethoxy, cyclopentylmethoxy, cyclohexylmethoxy or cycloheptylmethoxy, of which cyclopropylmethoxy, cyclobutylmethoxy and cyclopentylmethoxy are preferred.

3–7C-Cycloalkyl stands for cyclopropyl, cyclobutyl, cyclopentyl, cyclohexyl and cycloheptyl.

3–7C-Cycloalkylmethyl stands for methyl radical, which is substituted by one of the abovementioned 3–7C-cycloalkyl radicals. Examples which may be mentioned are the cyclopropylmethyl, the cyclopentylmethyl and the cyclohexylmethyl radicals.

3–7C-Alkenyl is a straight chain or branched alkenyl radical having 3 to 7 carbon atoms. Preferred examples are the 2-butenyl, 3-butenyl, 1-propenyl and the 2-propenyl (allyl) radicals.

3–7C-Alkinyl is a straight chain or branched alkynyl radical having 3 to 7 carbon atoms. Preferred examples are the 2-pentinyl, 2-butinyl, 3-butinyl and the 2-propinyl (propargyl) radicals.

7–10C-Polycycloalkyl stands for 7–10C-bicycloalkyl or 7–10C-tricycloalkyl radicals, such as for example, bornyl, norbornyl or adamantyl.

A Phenyl-3–4C-alkenyl radical is, for example, the phenylprop-1-en-3-yl radical.

Halogen within the meaning of the present invention is bromine, chlorine and fluorine.

1–4C-Alkylcarbonyl is a carbonyl group to which one of the abovementioned 1–4C-alkyl radicals is bonded. An example is the acetyl radical ($CH_3C(O)$—).

1–4C-Alkylcarbonyloxy radicals contain, in addition to the oxygen atom, one of the abovementioned 1–4C-alkylcarbonyl radicals. An example is the acetoxy radical ($CH_3C(O)$—O—).

A 1–4C-Alkylcarbonylamino radical is, for example, the acetamido radical (—NH—C(O)—$CH_3$).

1–4C-Alkoxycarbonyl is a carbonyl group to which one of the abovementioned 1–4C-alkoxy radicals is bonded. Examples are the ethoxycarbonyl ($CH_3CH_2O$—C(O)—) and the methoxycarbonyl ($CH_3O$—C(O)—) radicals.

Mono- or Di-1–4C-alkylaminocarbonyl radicals are, for example, the methylaminocarbonyl, the dimethylaminocarbonyl and the diethylaminocarbonyl radicals.

Mono- or Di-1–4C-alkylamino radicals are, for example, the methylamino, the dimethylamino and the diethylamino radicals.

Mono- or Di-1–4C-alkylaminosulfonyl stands for sulfonyl group to which one of the abovementioned mono- or di-1–4C-alkylamino radicals is bonded. Examples which may be mentioned are the methylaminosulfonyl, the dimethylaminosulfonyl and the ethylaminosulfonyl radical.

Hydroxy-1–4C-alkyl stands for one of the abovementioned 1–4C-alkyl radicals which is substituted by hydroxyl. Examples which may be mentioned are the hydroxymethyl radical, the 2-hydroxyethyl radical or the 3-hydroxypropyl radical.

Carboxy-1–4C-alkyl radicals are, for example, the carboxymethyl (—$CH_2COOH$) and the carboxyethyl (—$CH_2CH_2COOH$) radicals.

The groups —$C_mH_{2m}$—, —$C_nH_{2n}$—, —$C_pH_{2p}$— and —$C_qH_{2q}$— can be straight chain or branched groups. Examples which may be mentioned for the —$C_mH_{2m}$— group are the octylene, heptylene, isoheptylene (2-methylhexylene), hexylene, isohexylene (2-methylpentylene), neohexylene (2,2-dimethylbutylene), butylene, isobutylene, sec-butylene, tert-butylene, propylene, isopropylene, ethylene, 1-methylemthylene and the methylene group.

Examples which may be mentioned for the —$C_pH_{2p}$— group are the hexylene, isohexylene (2-methylpentylene), neohexylene (2,2-dimethylbutylene), butylene, isobutylene, sec-butylene, tert-butylene, propylene, isopropylene, ethylene, 1-methylmethylene and the methylene group.

Examples which may be mentioned for the —$C_mH_{2m}$— group are the butylene, isobutylene, sec-butylene, tert-butylene, propylene, isopropylene, ethylene, 1-methylmethylene and the methylene group.

Examples which may be mentioned for the —$C_qH_{2q}$— group are the ethylene, 1-methylmethylene and the methylene group. The group —$C_qH_{2q}$— represents a covalent bond in case of q is 0 (zero).

Aza-heterocycles which are component (Ar) of the group of substituents defined as —$C_pH_{2p}$—Ar and contain the grouping —NH— (imino), such as for example, pyrrole, imidazole, benzimidazole, benzotriazole or benzosuccinimide, are preferably bonded via their imino-nitrogen to the above defined —$C_pH_{2p}$— group.

Suitable salts for compounds of the formula I—depending on substitution—are all acid addition salts or all salts with bases. Particular mention may be made of the pharmacologically tolerable salts with the inorganic and organic acids and bases customarily used in pharmacy. Those suitable are, on the one hand, water-soluble and water-insoluble acid addition salts with acids such as, for example, hydrochloric acid, hydrobromic acid, phosphoric acid, nitric acid, sulphur acid, acetic acid, citric acid, D-gluconic acid, benzoic acid, 2-(4-hydroxybenzoyl)benzoic acid, and butyric acid, sulphosalicyclic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium potassium, calcium, aluminum, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

Compounds of the formula I to be emphasized are those in which

R1 is 1–4C-alkoxy or 1–2C-alkoxy which is completely or predominantly substituted by fluorine, R2 is 1–4C-alkoxy, 3–7C-cycloalkoxy, 3–7C-cycloalkylmethoxy or 1–2C-alkoxy which is completely or predominantly substituted by fluorine.

R3 and R4 are both hydrogen or together form an additional bond,

R5 is R6, —$C_mH_{2m}$—R7, —$C_nH_{2n}$—C(O)R8, —CH(R9)$_2$ or —$C_pH_{2p}$—Ar, in which R6 is hydrogen, 1–8C-alkyl, 3–8C-cycloalkyl, 3–7C-cycloalkylmethyl, 3–7C-alkenyl, 3–7C-alkynyl, phenyl-3–4C-alkenyl, bornyl, norbornyl, adamantyl, naphthyl, pyridyl, quinoxalinyl, indanyl, benzothiazolyl, N-methylpiperidyl, tetrahydropyranyl, tetrahydrothiopyranyl, or an unsubstituted or by R61 and/or 62 substituted phenyl radical, in which R61 is 1–2C-alkyl, 1–2C-alkoxy, nitro, halogen, carboxyl, carboxy-1–4C-alkyl, 1–4C-alkoxycarbonyl, hydroxy-1–4C-alkyl, amino, mono- or di-1–4C-alkylamino, aminocarbonyl, aminosulfonyl, mono- or di-1–4C-alkylaminosulfonyl, 4-methylphenylsulfonamido, tetrazol-5-yl, 2-(1–4C-alkyl)tetrazol-5-yl or 2-benzyltetrazol-5-yl, and R62 is 1–2C-alkyl, 1–2C-alkoxy, nitro or halogen, R7 is hydroxyl, halogen, carboxyl, nitroxy (—O—NO$_2$), phenoxy, carboxyphenyloxy, 1–4C-alkoxy, 1–4C-alkylcarbonyl, 1–4C-alkylcarbonyloxy, 1–4C-alkylcarbonylamino, 1–4C-alkoxycarbonyl, aminocarbonyl, mono- or di-1–4C-alkylaminocarbonyl, amino, mono- or di-1–4C-alkylamino, or an unsubstituted or by R71 and/or R72 substituted piperidyl, piperazinyl or morpholinyl radical, where R71 is hydroxyl, 1–4C-alkyl, 1–4C-hydroxyalkyl or 1–4C-alkoxycarbonyl, and R72 is 1–4C-alkyl, carboxyl, aminocarbonyl or 1–4C-alkoxycarbonyl, R8 is an unsubstituted or by R81 and/or R82 substituted phenyl or naphthyl radical, where R81 is hydroxyl, halogen, 1–4C-alkyl, 1–4C-alkoxy, 1–4C-alkylcarbonyloxy, 1–4C-alkylcarbonylamino, or 1–2C-alkoxy which is completely or predominantly substituted by fluorine, and R82 is halogen, 1–4C-alkyl or 1–4C-alkoxy, R9 is —$C_qH_{2q}$—phenyl, Ar is an unsubstituted phenyl, naphthyl, pyridyl, benzimidazolyl, benzoxazolyl, benzothiazolyl, benzotriazolyl, N-benzosuccinimidyl, imidazolyl, oxazolyl, thiazolyl, a 2-(1–2C-alkyl)-thiazol-4-yl radical, or a phenyl radical substituted by R10 and/or R11, in which R10 is hydroxyl, halogen, 1–4C-alkyl, trifluoromethyl, 1–4C-alkoxy, carboxyl, carboxy-1–4C-alkyl, 1–4C-alkylcarbonyloxy, 1–4C-alkoxycarbonyl and R11 is hydroxyl, halogen, 1–4C-alkyl or 1–4C-alkoxy, m is an integer from 1 to 8, n is an integer from 1 to 4, p is an integer from 1 to 6, q is an integer from 0 to 1, and the salts of these compounds.

Compounds of the formula I of embodiment a which are to be emphasized are those, in which R1 is 1–4C-alkoxy or 1–2C-alkoxy which is completely or predominantly substituted by fluorine, R2 is 1–4C-alkoxy, 3–7C-cycloalkoxy or 1–2C-alkoxy which is completely or predominantly substituted by fluorine, R3 and R4 are both hydrogen or together form an additional bond, R5 is R6, —$C_mH_{2m}$—R7, —$C_nH_{2n}$—C(O)R8, —CH(R9)$_2$ or —$C_pH_{2p}$—Ar, in which
R6 is hydrogen, 1–8C-alkyl, 3–7C-cycloalkyl, 3–7C-cycloalkylmethyl, 3–7C-alkenyl, 3–7C-alkynyl, phenyl-3–4C-alkenyl or an unsubstituted or by R61 and/or R62 substituted phenyl radical, in which
R61 is 1–2C-alkyl, 1–2C-alkoxy or halogen,
R62 is 1–3C-alkyl, nitro or halogen,
R7 is hydroxyl, carboxyl, phenoxy, 1–4C-alkoxy, 1–4C-alkylcarbonyl, 1–4C-alkylcarbonyloxy, 1–4C-alkylcarbonylamino, 1–4C-alkoxycarbonyl, aminocarbonyl, mono- or di-1–4C-alkylaminocarbonyl, amino, mono- or di-1–4-alkylamino, or an unsubstituted or by R71 and/or R72 substituted piperidyl, piperaznyl or morpholinyl radical, where
R71 is hydroxyl, 1–4C-alkyl, 1–4C-hydroxyalkyl or 1–4C-alkoxycarbonyl, and
R72 is 1–4C-alkyl, carboxyl, aminocarbonyl or 1–4C-alkoxycarbonyl,
R8 is an unsubstituted or by R81 and/or R82 substituted phenyl or naphthyl radical, where
R81 is hydroxyl, halogen, 1–4C-alkyl, 1–4C-alkoxy, 1–4C-alkylcarbonyloxy, 1–4C-alkylcarbonylamino or 1–2C-alkoxy which is completely or predominantly substituted by fluorine, and
R82 is halogen, 1–4C-alkyl or 1–4C-alkoxy,
R9 is —$C_qH_{2q}$—phenyl,
Ar is an unsubstituted phenyl, naphthyl, pyridyl, benzimidazolyl, benzoxazolyl, benzothiazolyl, benzotriazolyl, imidazolyl, oxazolyl, thiazolyl, a 2-(1–2C-alkyl)-thiazol-4-yl radical, or a phenyl radical substituted by R10 and/or R11, in which
R10 is hydroxyl, halogen, 1–4C-alkyl, trifluoromethyl, 1–4C-alkoxy, carboxyl, carboxy-1–4C-alkyl, 1–4C-alkylcarbonyloxy, 1–4C-alkoxycarbonyl and
R11 is hydroxyl, halogen, 1–4C-alkyl or 1–4C-alkoxy, and
m is an integer from 1 to 8,
n is an integer from 1 to 4,
p is an integer from 1 to 4,
q is an integer from 0 to 1,
and the salts of these compounds.

Compounds of the formula I which are particularly to be emphasized are those in which
R1 is methoxy, ethoxy or difluoromethoxy,
R2 is 1–4C-alkoxy, difluoromethoxy, 3–4C-cycloalkoxy or 3–5C-cycloalkylmethoxy,
R3 and R4 are both hydrogen or together form an additional bond,
R5 is R6, —$C_mH_{2m}$—R7, —$C_nH_{2n}$—C(O)R8, —CH(R9)$_2$ or —$C_pH_{2p}$—Ar, in which
R6 is hydrogen, 1–8C-alkyl, 3–8C-cycloalkyl, 3–7C-cycloalkylmethyl, 3–4C-alkenyl, 3–4C-alkynyl, phenyl-3–4C-alkenyl, adamantyl, pyridyl, quinoxalinyl, indanyl, benzothiazolyl, N-methylpipendyl, tetrahydropyranyl, tetrahydrothiopyranyl, an unsubstituted or by R61 and/or R62 substituted phenyl radical, in which
R61 is 1–2C-alkyl, 1–2C-alkoxy, nitro, halogen, carboxyl, carboxy-1–2C-alkyl, 1–4C-alkoxycarbonyl, hydroxy-1–2C-alkyl, amino, aminosulfonyl, 4-methylphenylsulfonamido, 2-(1–2C-alkyl)tetrazol-5-yl or 2-benzyltetrazol-5-yl, and
R62 is 1–2C-alkyl or halogen,
R7 is hydroxyl, halogen, carboxyl, nitroxy (—O—NO$_2$), phenoxy, carboxyphenyloxy, 1–4C-alkoxycarbonyl, aminocarbonyl, mono- or di-1–4C-alkylaminocarbonyl, amino, mono- or di-1–4-alkylamino, or an unsubstituted or by R71 and/or R72 substituted piperidyl, piperazinyl or morpholinyl radical, where
R71 is hydroxyl, 1–4C-alkyl, 1–4C-hydroxyalkyl or 1–4C-alkoxycarbonyl, and
R72 is 1–4C-alkyl, carboxyl, aminocarbonyl or 1–4C-alkoxycarbonyl,
R8 is an unsubstituted or by R81 substituted phenyl or naphthyl radical, where
R81 is halogen or 1–4C-alkoxy,
R9 is —$C_qH_{2q}$—phenyl,
Ar is an unsubstituted phenyl, naphthyl, pyridyl, benzimidazolyl, benzotriazolyl, N-benzosuccinimidyl, imidazolyl, thiazolyl, a 2-(1–2C-alkyl)-thiazol-4-yl-radical, or phenyl radical substituted by R10 and/or R11, in which
R10 is hydroxyl, halogen, 1–2C-alkyl, trifluoromethyl, 1–2-alkoxy, carboxyl, carboxy-1–2C-alkyl or 1–2C-alkoxycarbonyl, and
R11 is halogen, 1–2C-alkyl or 1–2C-alkoxy,
m is an integer from 1 to 8,
n is an integer from 1 to 6,
p is 1 or 2,
q is 0 or 1,
and the salts of these compounds.

Compounds of the formula I of embodiment a which are particularly to be emphasized are those, in which
R1 is methoxy, ethoxy or difluoromethoxy,
R2 is 1–4C-alkoxy, difluoromethoxy or 3–5C-cycloalkoxy,
R3 and R4 are both hydrogen or together form an additional bond,
R5 is R6, —$C_mH_{2m}$—R7, —$C_nH_{2n}$—C(O)R8, —CH(R9)$_2$ or —$C_pH_{2p}$—Ar, in which
R6 is hydrogen, 1–8C-alkyl, 3–7C-cycloalkyl, 3–7C-cycloalkylmethyl, 3–4C-alkenyl, 3–4C-alkynyl, phenyl-3–4C-alkenyl, or an unsubstituted or by R61 and/or R62 substituted phenyl radical, in which
R61 is 1–2C-alkyl, 1–2-alkoxy or halogen, and
R62 is 1–2C-alkyl or halogen,
R7 is hydroxyl, carboxyl, phenoxy, 1–4C-alkoxycarbonyl, aminocarbonyl, mono- or di-1–4-alkylaminocarbonyl, amino, mono- or di-1–4C-alkylamino, or an unsubstituted or by R71 and/or R72 substituted piperidyl, piperazinyl or morpholinyl radical, where
R71 is hydroxyl, 1–4C-alkyl, 1–4C-hydroxyalkyl or 1–4C-alkoxycarbonyl, and
R72 is 1–4C-alkyl, carboxyl, aminocarbonyl or 1–4C-alkoxycarbonyl,
R8 is an unsubstituted or by R81 substituted phenyl or naphthyl radical, where
R81 is halogen or 1–4C-alkoxy,
R9 is —$C_qH_{2q}$—phenyl,
Ar is an unsubstituted phenyl, naphthyl, pyridyl, benzotriazolyl, thiazolyl, a 2-(1–2C-alkyl)-thiazol-4-yl-radical, or a phenyl radical substituted by R10 and/or R11, in which
R10 is hydroxyl, halogen, 1–2C-alkyl, trifluoromethyl, 1–2C-alkoxy, carboxyl, carboxy-1–2C-alkyl or 1–2C-alkoxycarbonyl, and
R11 is halogen, 1–2C-alkyl or 1–2C-alkoxy,
m is an integer from 1 to 6,
n is 1 or 2,
p is 1 or 2,
q is 0 or 1,
and the salts of these compounds.

Preferred compounds of the formula I are those in which
R1 is methoxy or ethoxy,
R2 is methoxy, ethoxy, difluoromethoxy, cyclopropylmethoxy or cyclopentyloxy,
R3 and R4 are both hydrogen or together form an additional bond, R5 is R6, —$C_mH_{2m}$—R7, —$C_nH_{2n}$—C(O)R8, —CH(R9)$_2$ or —$C_pH_{2p}$—Ar, in which
R6 is hydrogen, 1–8C-alkyl, 3–8C-cycloalkyl, 3–7C-cycloalkylmethyl, allyl, 2-propinyl, phenyl-trans-prop-1-en-3-yl, adamantyl, pyridyl, quinoxalinyl, indanyl, benzothiazolyl, N-methylpiperidyl, tetrahydropyranyl, tetrahydrothiopyranyl, or an unsubstituted or by R61 substituted phenyl radical, in which
R61 is 1–4C-alkyl, nitro, halogen, carboxyl, carboxymethyl, hydroxy-1–2C-alkyl, amino, aminosulfonyl, 4-methylphenylsulfonamido, 2-ethyltetrazol-5-yl or 2-benzyltetrazol-5-yl,
R7 is hydroxyl, halogen, carboxyl, nitroxy (—O—NO$_2$), phenoxy, carboxyphenyloxy, 1–4C-alkoxycarbonyl, amino, methylamino, dimethylamino, dimethylaminocarbonyl, 1-piperidyl or N-methyl-4-piperidyl,
R8 is phenyl, 2-methoxyphenyl, 4-chlorophenyl or 2-naphthyl,
R9 is —$C_qH_{2q}$—phenyl,
Ar is an unsubstituted phenyl, pyridyl, benzimidazolyl, benzotriazolyl, N-benzosuccinimidyl, imidazolyl, a 2-methyl-thiazol-4-yl radical, or a phenyl radical substituted by R10 and/or R11, in which
R10 is hydroxyl, halogen, methoxy, trifluoromethyl, carboxyl, carboxymethyl or methoxycarbonyl, and
R11 is methoxy,
m is an integer from 1 to 8,
n is 1,
p is an integer from 1 to 6,
q is 0,
and the salts of these compounds.

Preferred compounds of the formula I of embodiment a are those, in which
R1 is methoxy or ethoxy,
R2 is methoxy, ethoxy or cyclopentyloxy,
R3 and R4 are both hydrogen or together form an additional bond,
R5 is R6, —$C_mH_{2m}$—R7, —$C_nH_{2n}$—C(O)R8, —CH(R9)$_2$ or —$C_pH_{2p}$—Ar, in which
R6 is hydrogen, 1–6C-alkyl, 3–7C-cycloalkyl, 3–7C-cycloalkylmethyl, allyl, 2-propinyl, phenyl, or phenyl-tran-prop-1-en-3-yl,
R7 is hydroxyl, carboxyl, phenoxy, 1–4C-alkoxycarbonyl, dimethylamino, dimethylaminocarbonyl, 1-piperidyl or N-methyl-4-piperidyl,
R8 is phenyl, 2-methoxyphenyl, 4-chlorophenyl or 2-naphthyl,
R9 is —$C_qH_{2q}$—phenyl,
Ar is an unsubstituted phenyl, pyridyl, benzotriazolyl, a 2-methyl-thiazol-4-yl radical, or a phenyl radical substituted by R10 and/or R11, in which
R10 is hydroxyl, halogen, methoxy, trifluoromethyl, carboxyl, carboxymethyl or methoxycarbonyl, and
R11 is methoxy,
m is an integer from 1 to 6,
n is 1,
p is 1 or 2,
q is 0,
and the salts of these compounds.

Especially preferred compounds of the formula I are those in which
R1 is methoxy,
R2 is methoxy, ethoxy, difluoromethoxy, cyclopropylmethoxy or cyclopentyloxy,
R3 and R4 are both hydrogen or together form an additional bond,
R5 is R6, —$C_nH_{2n}$—C(O)R8 or —$C_pH_{2p}$—Ar, in which
R6 is 3–8C-alkyl, 5–8-cycloalkyl, 3–7C-cycloalkylmethyl, adamantyl, quinoxalinyl, indanyl, benzothiazolyl, tetrahydropyranyl, tetrahydrothiopyranyl, or an unsubstituted or by R61 substituted phenyl radical, in which
R61 is 1–4C-alkyl, nitro, halogen, carboxyl, carboxymethyl, hydroxy-1–2C-alkyl, aminosulfonyl, 4-methylphenylsulfonamido, 2-ethyltetrazol-5-yl or 2-benzyltetrazol-5-yl,
R8 is phenyl or 2-naphthyl,
Ar is an unsubstituted phenyl, benzimidazolyl, N-benzosuccinimidyl, imidazolyl, or a phenyl radical substituted by R10, in which
R10 is hydroxyl, halogen, methoxy, trifluoromethyl or carboxyl,
n is 1,
p is an integer from 1 to 6,
and the salts of these compounds.

Especially preferred compounds of the formula I of embodiment a are those, in which
R1 is methoxy or ethoxy,
R2 is methoxy, ethoxy or cyclopentyloxy,
R3 and R4 are both hydrogen or together form an additional bond,
R5 is R6, —$C_mH_{2m}$—R7, —$C_nH_{2n}$—C(O)R8, or —$C_pH_{2p}$—Ar, in which
R6 is 1–6C-alkyl, 3–7C-cycloalkyl, 3–7C-cycloalkylmethyl, allyl, 2-propinyl, phenyl or phenyl-trans-prop-1-en-3-yl,
R7 is hydroxyl, carboxyl or phenoxy,
R8 is phenyl, 2-methoxyphenyl, 4-chlorophenyl or 2-naphthyl,
R9 is —$C_qH_{2q}$—phenyl,
Ar is an unsubstituted phenyl, pyridyl, benzotriazolyl, a 2-methyl-thiazol-4-yl radical, or a phenyl radical substituted by R10 and/or R11, in which
R10 is hydroxyl, halogen, methoxy, trifluoromethyl, carboxyl, carboxymethyl or methoxycarbonyl, and
R11 is methoxy,
m is an integer from 1 to 6,
n is 1,
p is 1 or 2,
q is 0,
and the salts of these compounds.

The compounds of formula I are chiral compounds with chiral centers in the positions 4a and 8a

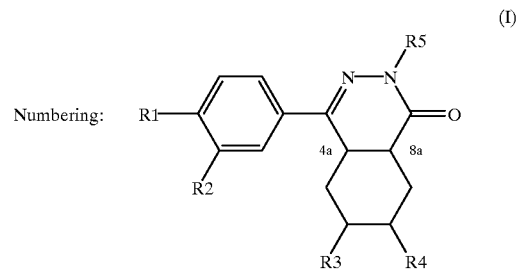

Numbering:

Therefore the invention includes all conceiveable pure diasteromers and pure enantiomers, as well all mixtures thereof independent from the ratio, including the racemates. Preferred are those compounds, in which the hydrogen atoms in the positions 4a and 8a are cis-configurated. Especially preferred in this connection are those compounds, in which the absolute configuration (according to the rules of Cahn, Ingold and Prelog) is S in the position 4a and R in the position 8a. Racemates can be split up into the corresponding enantiomers by methods known by a person skilled in the art. Preferably the racemic mixtures are separated into two diasteromers with the help of an optical active separation agent on the stage of the cyclohexanecarboxylic acids (starting compounds A, B, D and G) or the 1,2,3,6-tetrahydrobenzoic acids (starting compounds C, E and F). As separation agents may be mentioned, for example, optical active amines such as the (+)- and (−)-forms of α-phenylethylamin and ephedrine, or the optical active alkaloids cinchonine, cinchonidine and brucine.

The invention further relates to a process for the preparation of compounds of formula I and their salts.

The process comprises a) reacting keto acids of formula II

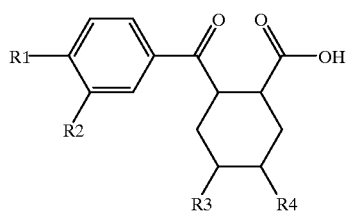

(II)

or one of their reactive derivatives in which R1, R2, R3 and R4 have the abovementioned meanings in the first step with hydrazine hydrate to compounds of formula I

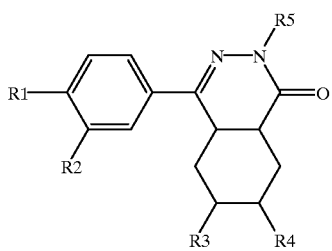

(I)

in which R1, R2, R3 and R4 have the abovementioned meanings and R5 stands for hydrogen (H).

If desired, these compounds can be reacted with alkylating agents of formula R5-X, in which R5 has the abovementioned meanings [exception: R5 does not represent hydrogen (H)] and X represents a leaving group to give further compounds of formula I, in which R1, R2, R3, R4 and R5 have the abovementioned meanings [exception: R5 does not represent hydrogen (H)].

b) reacting, alternatively to procedure a), keto acids of formula II or one of their reactive derivatives, in which R1, R2, R3 and R4 have the abovementioned meanings with suitable hydrazine derivates of formula R5—NH—NH₂, in which R5 has the abovementioned meanings [exception: R5 does not represent hydrogen (H)], to give compounds of the formula I, in which R1, R2, R3, R4 and R5 have the abovementioned meanings [exception: R5 does not represent hydrogen (H)].

The conversion of the keto acids of formula II or one of their reactive derivatives with hydrazine hydrate [according to procedure a)] respectively with suitable hydrazine-derivates of the formula R5—NH—NH₂ [according to procedure b)] is advantageously carried out with one to five equivalents of hydrazine hydrate respectively the suitable hydrazine derivates of formula R5—NH—NH₂, which simultaneously can be used as solvent. More suitable is, however, to use an additional appropriate solvent. As inert solvents are preferably used alcohols such as methanol, ethanol, isopropanol, n-butanol, isoamylalcohol, glycols and their ethers such as ethylene glycol, diethylene glycol, ethylene glycol, monomethyl or monoethyl ether, carboxylic acids, such as formic acid, acetic or propionic acid, suitable mixtures of the abovementioned solvents, as well as mixtures with water, for example aqueous ethanol, further ethers, especially water soluble ethers such as tetrahydrofuran, dioxane or ethylene glycol dimethylether; further toluene or benzene, especially when the method of azeotropic destillation is used to remove the reaction water.

The reaction temperatures are suitably between 0 and 200° C., preferably between 20 and 100° C.; the reaction times are preferably between 1 and 48 hours.

Suitable reactive derivatives of the keto acids of formula II which may be mentioned in this context are, for example, esters, especially methyl and ethyl esters, nitrils and acid halides, such as acid chlorides or acid bromides. They can be prepared, for example, starting from the corresponding keto acids of formula II, by methods which are known by the person skilled in the art.

The conversion of compounds of formula I, in which R1, R2, R3 and R4 have the abovementioned meanings and R5 represents hydrogen (H) with alkylating agents of the formula R5—X, in which R5 has the abovementioned meanings [with the exception of hydrogen (H)] and X represents a suitable leaving group, is carried out in a manner, which is known by a person skilled in the art.

In a first step, the hydrogen atom (H) of the NH-group of the compounds of formula I, in which R5 represents a hydrogen atom (H) is removed by a base such as, for example, potassium carbonate, sodium hydroxide, sodium hydride, sodium methanolate, sodium ethanolate or buthylithium in a suitable inert solvent such as dimethylformamide, dimethylsulfoxide, tetrahydrofuran or diethylether. The alkylation is then carried out by adding an appropriate alkylating agent of the formula R5—X.

The bases are preferably used in more than an equimolar ratio; the reaction temperature is preferably between 0 and 150° C.

Examples of suitable leaving groups X which may be mentioned are halogen atoms, especially chlorine, or hydroxyl groups activated by esterification (for example with p-toluenesulfonic acid).

Suitable alkylating agents of the formula R5—X are for example iodomethane, bromoethane, 1-bromopropane, 2-bromopropane, 1-bromohexane, 3-bromopentane, cyclopentylbromide, bromomethylcyclohexane, chloromethylcyclopropane, cycloheptylbromide, allylchloride, propargylbromide, 3-bromo-1-propanol, 6-bromohexanoic acid, 8-bromooctanoic acid, 2-bromethyl-N,N-dimethylamine, ethylbromoacetate, 4-chloro-N-methylpiperidine, ω-bromoacetophenone, diphenylchloromethane, 3-phenoxy-1-bromopropane, 1,4-dibromobutane, 1,6-dibromohexane, ω-bromo-4-chloroacetophenone, ω-bromo-2-methoxyacetophenone, α-bromo-2'-acetonaphthone, 4-chloromethylbenzoic acid, 3-bromomethylbenzoic acid, 4-chloromethylphenylacetic acid, benzylchloride, 2-methoxybenzylchloride, 3-methoxybenzylchloride, 4-methoxybenzylchloride, 3,5-dimethoxybenzylchloride, 2-trifluoromethylbenzylchloride, 2-chlorobenzylchloride, 2-picotylchloride, 3-picotylchloride, 4-picotylchloride, 4-chloromethyl-2-methylthiazole, 1-bromomethylbenztriazole, 2-bromoethylbenzene, 3-phenyl-2-[trans]propenylchloride, 4-benzyloxybenzylchloride and 2-benzyloxybenzylchloride.

Examples of suitable hydrazine-derivates of formula R5—NH—NH$_2$ are methylhydrazine, 4-heptylhydrazine, cyclohexylhydrazine, cyclooctylhydrazine, adamantylhydrazine, 2-hydroxyethylhydrazine, 4-tert-butylhydrazine, phenylhydrazine, 2-methylphenylhydrazine, 4-tert-butylphenylhydrazine, 2-chlorophenylhydrazine, 3-hydrazinobenzoic acid, 4-hydrazinophenylacetic acid, 2-(4-hydrazinophenyl) ethanol, 4-sulfonamidophenylhydrazine, 4-nitrophenylhydrazine, 4-(2-ethyltetrazol-5-yl) phenylhydrazine, 2-benzyl-5-(4-hydrazinophenyl)tetrazole, benzylhydrazine, 2-bromophenylhydrazine, 4-chlorophenylhydrazine, 4-fluorophenylhydrazine, 2,4-dichlorophenylhydrazine, 4-chloro-o-tolylhydrazine, 2,5-dimethylphenylhydrazine, 2,4-dinitrophenylhydrazine, 4-methoxyphenylhydrazine, 3-nitrophenylhydrazine, p-tolylhydrazine, 2-pyridylhydrazine, 2-indanylthydrazine, 2-hydrazino-1,4-benzodiazine, 2-hydrazinobenzothiazole, 4-hydrazinotetrahydropyran and 4-hydrazinotetrahydrothiopyran.

Keto acids of the formula II, in which R1, R2, R3 and R4 have the abovementioned meanings can, for example, be prepared from compounds of the formula III.

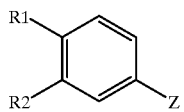

(III)

in which R1 and R2 have the abovementioned meanings and Z represents hydrogen (H) by Friedel-Crafts acylation with compounds of the formula IV,

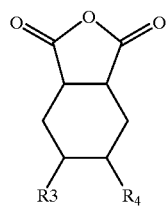

(IV)

in which R3 and R4 have the abovementioned meanings. The Friedel-Crafts acylation is carried out in a manner which in known by the skilled person (for example as described in M. Yamaguchi et al., J. Med. Chem. 36: 4052–4060, 1993) in presence of a suitable catalyst, such as for example, AlCl$_3$, ZnCl$_2$, FeCl$_3$ or iodine, in an appropriate inert solvent, such as methylene chloride or nitrobenzene or another inert solvent such as diethylether, preferably at raised temperature, especially at the boiling point of the solvent being used.

Alternatively, the compounds of formula II, in which R1, R2, R3 and R4 have the abovementioned meanings, can be prepared from compounds of the formula III, in which R1 and R2 have the abovementioned meanings and Z represents a halogen atom through reaction with compounds of the formula IV, in which R3 and R4 have the abovementioned meanings.

The reaction, which is mentioned in the previous paragraph is carried out in a manner which is known by a person skilled in the art, for example a) by activating compounds of formula III, in which R1, R2 and Z have the abovementioned meanings, by a lithium/halogen exchange reaction at low temperatures (preferably at −60 to −100° C.) in an appropriate inert solvent such as tetrahydrofuran or diethylether, preferably under an atmosphere of inert gas, followed by reaction of the lithiated compounds with cyclic carboxylic acid anhydrides of formula IV, or b) by converting compounds of formula III in which R1, R2 and Z have the abovementioned meanings, in a suitable inert solvent such as, for example, tetrahydrofuran or diethylether into the corresponding Grignard compounds of formula III in which Z represents MgCl, MgBr or MgI followed by reaction of the Grignard compounds with cyclic carboxylic acid anhydrides of formula IV, in which R3 and R4 have the abovementioned meanings.

Compounds of formula III, in which R1 and R2 have the abovementioned meanings and Z represents a hydrogen (H) or halogen atom, are known or can be prepared by methods known by a person skilled in the art.

Compounds of formula IV, in which R3 and R4 have the abovementioned meanings are as well known or can be prepared by methods known by a person skilled in the art.

Additionally, it is possible to convert one functional group of a compound of formula I to another functional group by customary methods and reactions.

Thus, if desired, compounds of formula I with suitable functional groups can be converted into further compounds of formula I.

For instance, compounds of formula I, in which R5 comprises an ester can be converted by acidic or alkaline saponification to the corresponding carboxylic acid or by reaction with a suitable amine to the corresponding amide.

Furthermore, compounds of formula I, in which R5 comprises a reactive leaving group such as, for example, a halogen atom, can be converted to the corresponding amines by reaction with an appropriate amine.

Additionally, compounds of formula I, in which R2 comprises an acid labile ether bond, such as for example, the cyclopentyl-oxygen bond, can be converted by an acidic ether cleavage reaction into compounds of formula I, in which R2 represents a hydroxyl group. The renewed alkylation of this hydroxyl group with appropriate alkylation reagents leads to further compounds of formula I.

As appropriate alkylation reagents may be mentioned in this context, for example, chlorodifluoromethane or cyclopropylmethylchloride.

Suitably, the conversions are carried out analogous to methods which are familiar per se to the person skilled in the art, for example, in the manner which is described in the following examples.

The substances according to the invention are isolated and purified in a manner known per se, e.g. by distilling off the solvent in vacuo and recrystallizing the residue obtained from a suitable solvent or subjecting it to one of the customary purification methods, such as column chromatography on a suitable support material.

Salts are obtained by dissolving the free compound in a suitable solvent, e.g. in a chlorinated hydrocarbon, such as methylene chloride or chloroform, or a low molecular weight aliphatic alcohol (ethanol, isopropanol) which contains the desired acid or base, or to which the desired acid or base is then added. The salts are obtained by filtering, reprecipitating, precipitating with a non-solvent for the addition salt or by evaporating the solvent. Salts obtained can be converted by basification or by acidifying into the free compounds which, in turn, can be converted into salts. In this manner, pharmacologically non-tolerable salts can be converted into pharmacologically tolerable salts.

The following examples illustrate the invention in greater detail, without restricting it. As well, further compounds of formula I, of which the preparation is explicitly not described, can be prepared in an analogous way or in a way which is known by person skilled in the art using customary preparation methods.

In the examples stand M.p. for melting point, min for minutes and THF for tetrahydrofuran. The compounds, which are mentioned in the examples as well as their salts are preferred compounds of the invention.

EXAMPLES

Final Products 1. (cis)-4-(3,4-Dimethoxyphenyl)-4a,5,6,7,8,8a-hexahydro-2H-phthalazin-1-one A solution of 26 g of compound A (see starting compounds) and 19 g of hydrazine hydrate was refluxed for 4 hours in ethanol. After cooling to room temperature, the precipitate was filtered off and dried. M.p. 170° C.

2. (trans)-4-(3,4-Dimethoxyphenyl)-4a,5,6,7,8,8a-hexahydro-2H-phthalazin-1-one

Prepared from compound B (see starting compounds) and hydrazine hydrate as described for compound 1. M.p. 143–146° C.

3. (cis)-4-(3,4-Dimethoxyphenyl)-4a,5,8,8a-tetrahydro-2H-phthalazin-1-one

Prepared from hydrazine hydrate and compound C (see starting compounds) as described for compound 1. M.p. 173–174° C.

4. (cis)-4-(3-Cyclopentyloxy-4-methoxyphenyl)-4a,5,6,7,8,8a-hexahydro-2H-phthalazin-1-one Prepared from compound D (see starting compounds) and hydrazine hydrate as described for compound 1. M.p. 175–176° C.

5. (cis)-4-(3-Cyclopentyloxy-4-methoxyphenyl)-4a,5,8,8a-tetrahydro-2H-phthalazin-1-one Prepared from compound E (see starting compounds) and hydrazine hydrate as described for compound 1. M.p. 166–168° C.

6. (cis)-4-(3-Ethoxy-4-methoxyphenyl)-4a,5,8,8a-tetrahydro-2H-phthalazin-1-one

Prepared from compound F (see starting compounds) and hydrazine hydrate as described for compound 1. M.p. 163–166° C.

7. (cis)-4-(3,4-Diethoxyphenyl)-4a,5,6,7,8,8a-hexahydro-2H-phthalazin-1-on

Prepared from compound G (see starting compounds) and hydrazine hydrate as described for compound 1. Purified by chromatography (dichloromethane). Crystallized from ethyl acetate. M.p. 156–157° C.

8. (cis)-4-(3,4-Dimethoxyphenyl)-2-methyl-4a,5,6,7,8,8a-hexahydro-2H-phthalazin-1-one 6 mmol of a 60% suspension of sodium hydride in mineral oil was added to a suspension of 5 mmol of compound 1 in about 40 ml of dimethylformamide, under a flow of nitrogen at room temperature. After stirring this mixture for 30 minutes, 7 mmol of iodomethane was added and the resulting mixture was stirred for another 4 hours, after which the solvent was evaporated. The residue was partitioned between ethyl acetate and water, the organic layer was dried over magnesium sulfate and evaporated. The residue was purified by chromatography (dichloromethane). Crystallized from petroleum ether (60–95° C.). M.p. 110–112° C.

9. (cis)-4-(3,4-Dimethoxyphenyl)-2-ethyl-4a,5,6,7,8,8a-hexahydro-2H-phthalazin-1-one Prepared from compound 1 and bromoethane as described for compound 8. Crystallized from methanol. M.p. 105–106° C.

10. (cis)-4-(3,4-Dimethoxyphenyl)-2-(n-propyl)-4a,5,6,7,8,8a-hexahydro-2H-phthalazin-1-one Prepared from compound 1 and 1-bromopropane as described for compound 6. Purified by chromatography (dichloromethane). Crystallized from petroleum ether (60–95° C.). M.p. 95–96° C.

11. (cis)-4-(3,4-Dimethoxyphenyl)-2-(n-hexyl)-4a,5,8,8a-tetrahydro-2-H-phthalazin-1-one Prepared from compound 3 and 1-bromohexane as described for compound 8. Purified by chromatography; crystallized from petroleum ether (60–80° C.) at −20° C. M.p. 74–75° C.

12. (cis)-2-isopropyl-4-(3,4-dimethoxyphenyl)-4a,5,6,7,8,8a-hexahydro-2H-phthalazin-1-one Prepared from compound 1 and 2-bromopropane as described for compound 8. Purified by chromatography (dichloromethane). Crystallized from diethyl ether/petroleum ether (60–95° C.). M.p. 79–81° C.

13. (cis)-4-(3,4-Diemthoxyphenyl)-2-isopropyl-4a,5,8,8a-tetrahydro-2H-phthalazin-1-one Prepared from compound 3 and 2-bromopropane as described for compound 8. Crystallized and recrystallized from methanol. M.p. 146–149° C.

14. (cis)-4-(3,4-Dimethoxyphenyl)-2-(tert-butyl)-4a,5,6,7,8,8a-hexahydro-2H-phthalazin-1-one A mixture of 2 g of compound A (see starting compounds), 5 g of t-butylhydrazine and 5 ml of triethylamine in toluene was heated for 20 hours in a Dean-Stark apparatus. Purified by chromatography (dichloromethane) and crystallized from petroleum ether (60–95° C.) at −20° C. M.p. 99–101° C.

15. (cis)-2-(3-Ethyl-propyl)-4-(3,4-diethoxyphenyl)-4a,5,6,7,8,8a-hexahydro-2H-phthalazin-1-one Prepared from compound 1 and 3-bromopentane as described for compound 8. Purified by chromatography (dichloromethane). Crystallized from methanol. M.p. 98–99° C.

16. (cis)-2-(4-Propyl-butyl)-4-(3,4-dimethoxyphenyl)-4a,5,8,8a-tetrahydro-2H-phthalazin-1-one Prepared from compound 3 and 4-heptylhydrazine as described for compound 8. Purified by chromatography and crystallized from petroleum ether (60–80° C.) M.p. 71–73° C.

17. (cis)-4-(3,4-Diethoxyphenyl)-2-cyclopentyl-4a,5,6,7,8,8a-hexahydro-2H-phthalazin-1-one Prepared from compound 1 and cyclopentylbromide as described for compound 8. Crystallized from methanol. M.p. 111–114° C.

18. (cis)-4-(3,4-Dimethoxyphenyl)-2-cyclopentyl-4a,5,8,8a-tetrahydro-2H-phthalazin-1-one Prepared from compound 3 and cycloheptylbromide as described for compound 8. Purified by chromatography (dichloromethane) and crystallized from diethyl ether. M.p. 131–133° C.

19. (cis)-4-(3-Ethoxy-4-methoxyphenyl)-2-cyclopentyl-4a,5,8,8a-tetrahydro-2H-phthalazin-1-one A solution of 0.5 g of compound 6, 0.8 g of $K_2CO_3$ and 0.3 g of ethyliodide was stirred in 20 ml of N-methylpyrrolidinone for 4 h at 70° C. After cooling to room temperature, the reaction mixture was poured into 200 ml of water and this mixture was extracted with diethyl ether. After drying over magnesium sulfate, the solvent was evaporated and the compound crystallized from methanol, M.p. 124–127° C.

20. (cis)-4-(3-Difluoromethoxy-4-methoxyphenyl)-2-cyclopentyl-4a,5,8,8a-tetrahydro-2H-phthalazin-1-one A solution of 1 g of compound H, 0.06 g of tetraethylammonium bromide and 0.36 g of sodium hydroxide in 0.5 ml of water in 7 ml of dioxane at 80° C. was saturated for 30 min with chlorodifluoromethane. After cooling to room temperature, the dioxane was decanted and evaporated. The residue was partitioned between water and ethyl acetate. The organic layer was dried over magnesium sulfate and evaporated. The residue was purified by chromatography. Crystallization from petroleum ether (60–80° C.) M.p. 124–125° C.

21. (cis)-4-(3-Cyclopentyloxy-4-methoxyphenyl)-2-cyclopentyl-4a,5,8,8a-tetrahydro-2H-phthalazin-1-one Prepared from compound 5 and cyclopentylbromide as described for compound 8. Crystallized from diethyl ether. M.p. 144–145° C.

22. (cis)-4-(3,4-Diethoxyphenyl)-2-cyclohexyl-4a,5,8,8a-tetrahydro-2H-phthalazin-1-one Prepared from compound C (see starting compounds) and cyclohexylthydrazine as described for compound 35. Crystallized from methanol. M.p. 147–148° C.

23. (cis)-4-(3,4-Diemthoxyphenyl)-2-cycloheptyl-4a,5,6,7,8,8a-hexahydro-2H-phthalazin-1-one Prepared from compound 1 and cycloheptylbromide as described for compound 8. Crystallized from methanol. M.p. 102–104° C.

24. (cis)-4-(3-Cyclopentyloxy-4-methoxyphenyl)-2-cycloheptyl-4a,5,6,7,8,8a-hexahydro-2H-phthalazin-1-one Prepared from compound 4 and cycloheptylbromide as described for compound 8. Crystallized from petroleum ether (60–80° C.) M.p.111–112° C.

25. (cis)-4-(3,4-Diethoxyphenyl)-2-cycloheptyl-4a,5,8,8a-tetrahydro-2H-phthalazin-1-one Prepared from compound 3 and cycloheptylbromide as described for compound 105. Crystallized from methanol. M.p. 92–93° C.

26. (cis)-4-(3-Cyclopentyloxy-4-methoxyphenyl)-2-cycloheptyl-4a,5,8,8-tetrahydro-2H-phthalazin-1-one Prepared from compound 5 and cycloheptylbromide as described for compound 8. Crystallized from petroleum ether (60–80° C.). M.p. 106° C.

27. (cis)-4-(3-Cyclopropylmethoxy-4-methoxyphenyl)-2-cycloheptyl-4a,5,8,8a-tetrahydro-2H-phthalazin-1-one A mixture of 1.4 g of compound I, 0.4 g of cyclopropylmethylchloride, 1.1 g of potassium iodide and 0.6 g of $K_2CO_3$ were stirred in N-methyl-pyrrolidinone for 5 days at 60° C. Then the mixture was partitioned between water and diethyl ether. The organic layer was dried over magnesium sulfate and evaporated. Purification by chromatography (petroleum ether/ethyl acetate, 4:1). Crystallization from petroleum ether (60–80° C.). M.p. 102–103° C.

28. (cis)-4-(3-Difluoromethoxy-4-methoxyphenyl)-2-cycloheptyl-4a,5,8,8a-tetrahydro-2H-phthalazin-1-one Prepared from compound I as described for compound 20. Crystallized from dichloromethane/petroleum ether (60–80° C.). M.p. 83° C.

29. (cis)-4-(3,4-Dimethoxyphenyl)-2-cyclooctyl-4a,5,8,8a-tetrahydro-2H-phthalazin-1-one Prepared from compound 3 and cyclooctylhydrazine as described for compound 35. Purified by chromatography (dichloromethane) and crystallized from petroleum ether (40–60° C.). M.p. 75–77° C.

30. (cis)-4-(3,4-Dimethoxyphenyl)-2-adamantyl-4a,5,8,8a-tetrahydro-2H-phthalazin-1-one Prepared from compound 3 and adamantylhydrazine as described for compound 35. Crystallized from methanol. M.p. 157–159° C.

31. (cis)-4-(3,4-Diethoxyphenyl)-2-cyclopropylmethyl-4a,5,8,8a-tetrahydro-2H-phthalazin-1-one Prepared from compound 3 and chloromethylcyclopropane as described for compound 8. Crystallized from diethyl ether and recrystallized from methanol. M.p. 142–145° C.

32. (cis)2-Cyclohexylmethyl-4-(3,4-dimethoxyphenyl)-4a,5,6,7,8,8a-hexahydro-2H-phthalazin-1-one Prepared from compound 1 and bromomethylcyclohexane as described for compound 8. Purified by chromatography (dichloromethane). Crystallized from petroleum ether (60–95° C.). M.p. 137–139° C.

33. (cis)-2-Allyl-4-(3,4-dimethoxyphenyl)-4a,5,6,7,8,8a-hexahydro-2H-phthalazin-1-one Prepared from compound 1 and allylchloride as described for compound 8. Purified by chromatography (dichloromethane). Crystallized from petroleum ether (60–95° C.). M.p. 99–101° C.

34. (cis)-4-(3,4-Dimethoxyphenyl)-2-propargyl-4a,5,6,7,8,8a-hexahydro-2H-phthalazin-1-one Prepared from compound 1 and propargylbromide as described for compound 8, using sodium ethanolate instead of sodium hydride. Purified by chromatography (dichloromethane). Crystallized from methanol. M.p. 118–121° C.

35. (cis)-4-(3,4-Dimethoxyphenyl)-2-(2-hydroxy-1-ethyl)-4a,5,6,7,8,8a-hexahydro-2H-phthalazin-1-one A solution of 2 g of compound A (see starting compounds) and 2 g of 2-hydroxyethylhydrazine in a mixture of 100 ml of 1-propanol and 5 ml of triethylamine was refluxed for 18 h. After evaporating the solvent, the residue was partitioned between aqueous sodium carbonate and ethyl acetate. The compound was crystallized from diethyl ether and recrystallized from methanol (−20° C.). M.p. 128–129° C.

36. (cis)-2-(3-Hydroxy-1-propyl)-4-(3,4-dimethoxyphenyl)-4a,5,6,7,8,8a-hexahydro-2H-phthalazin-1-one Prepared from compound 1 and 3-bromo-1-propanol as described for compound 8. Purified by chromatography (dichloromethane). Crystallized from diethyl ether/ petroleum ether (60–95° C.). M.p. 94–97° C.

37. Ethyl-(cis)-4-(3,4-dimethoxyphenyl)-1-oxo-4a,5,6,7,8,8a-hexahydro-1H-phthalazin-2-yl)acetic acid.

Prepared from compound 1 and ethyl bromoacetate as described for compound 8. Crystallized from ethanol at −20° C. M.p. 97–99° C.

38. (cis)-4-(3,4-Diemthoxyphenyl)-1-oxo-4a,5,6,7,8,8a-hexahydro-1H-phthalazin-2-yl)acetic acid 1.5 g of compound 37 in a mixture of 200 ml of 2N NaOH, 100 ml of THF and 100 ml of methanol was stirred for 3 hours at room temperature. After removal of the organic solvents under reduced pressure, the solution was acidified with hydrochloric acid and extracted with ethyl acetate. The organic solution was dried over magnesium sulfate and evaporated. The compound was crystallized from acetone/petroleum ether (60–95° C.). M.p. 183–187° C.

39. (cis)06-(4-(3,4-Dimethoxyphenyl)-1-oxo-4a,5,6,7,8,8a-hexahydro-1H-phthalazin-2-yl)hexanoic acid sodium-salt Prepared from compound 1 and 6-bromohexanoic acid as described for compound 8, using 12 mmol of sodium hydride instead of 6 mmol. After evaporating the reaction mixture the residue was partitioned between aqueous sodium carbonate and ethyl acetate. The aqueous solution was acidified with hydrochloric acid and extracted with ethyl acetate. The organic layer was dried over magnesium sulfate and evaporated. Purified by chromatography (ethyl acetate). The compound (oil) was dissolved in diethyl ether. After addition of a concentrated solution of sodium-ethanolate, the precipitate was filtered off and crystallized from methanol/ether. M.p. 140–143° C.

40. (cis)-6-(4-(3,4-Diethoxyphenyl)-1-oxo-4a,5,8,8a-tetrahydro-1H-phthalazin-2-yl)hexanoic acid Prepared from compound 3 and 6-bromohexanoic acid as described for compound 39. Purified by chromatography and crystallized from ether at −20° C. M.p. 97–99° C.

41. (cis)-6-(4-(3,4-Diethoxyphenyl)-1-oxo-4a,5,6,7,8,8a-hexahydro-1H-phthalazin-2-yl)octanoic acid Prepared from compound 1 and 8-bromooctanoic acid as described for compound 39. Purified by chromatography. M.p. 90–91° C.

42. (cis)-4-(3,4-dimethoxyphenyl)-2-(6-bromo-1-hexyl)-4a,5,6,7,8,8a-hexahydro-2H-phthalazin-1-one Prepared from compound 1 and 1,6-dibromohexane as described for compound 58. Purified by chromatography [ethyl acetate/petroleum ether (60–80° C.), 1:2]. Crystallized from petroleum ether (60–80° C.). M.p. 74–75° C.

43. (cis)-4-(3,4-Dimethoxyphenyl)-2-(6-amino-1-hexyl)-4a,5,6,7,8,8a-hexahydro-2H-phthalazin-1-one fumarate A solution of 5 g of compound 42 in a mixture of 200 ml of methanol and 100 ml of tetrahydrofuran was saturated with ammonia and left for one week at room temperature. After evaporating the solvent, the residue was partitioned between aqueous sodium carbonate and ethyl acetate. The organic layer was evaporated and the compound crystallized as the fumarate from methanol/ethyl acetate. M.p. 127–129° C.

44. (cis)-4-(3,4-Dimethoxyphenyl)-2-(4-aminomethyl-1-butyl)-4a,5,6,7,8,8a-hexahydro-2H-phthalazin-1-one hemifumarate Prepared from compound 58 and methylamine as described for compound 46. Purified by chromatography and crystallized as the hemifumarate from ethyl acetate. M.p. 108–111° C.

45. (cis)-4-(3,4-Dimethoxyphenyl)-2-(2-dimethylaminoethyl)-4a,5,6,7,8,8a-hexahydro-2H-phthalazin-1-one fumarate Prepared from compound 1 and 2-bromethyl-N,N-dimethylamine hydrobromide as described for compound 8, using 12 mmol of sodium hydride instead of 6 mmol. Purified by chromatography (ethyl acetate). Crystallized as the fumarate from ether. M.p. 74–76° C.

46. (cis)-4-(3,4-Dimethoxyphenyl)-2-(4-dimethylamino-1-butyl)-4a,5,6,7,8,8a-hexahydro-2H-phthalazin-1-one fumarate A solution of 2 g of compound 58 in 50 ml of a 30% solution of dimethylamine in ethanol was left for 18 hours at room temperature. After evaporating this mixture the residue was purified by chromatography (ethyl acetate) and the compound was crystallized from ether as the fumarate. M.p. 119–121° C.

47. (cis)-4-(3,4-Dimethoxyphenyl)-2-(6-dimethylamino-1-hexyl)-4a,5,6,7,8,8a-hexahydro-2H-phthalazin-1-one oxalate Prepared from compound 42 as described for compound 46. Crystallized from acetone as the oxalate. M.p. 65–67° C.

48. (cis)-4-(3,4-Dimethoxyphenyl)-2-(4-(1-piperidyl)-1-butyl)-4a,5,6,7,8,8a-hexahydro-2H-phthalazin-1-one hydrochloride Prepared from compound 58 and piperidine (instead of dimethylamine) as described for compound 46. Purified by chromatography (ethyl acetate). Crystallized as the hydrochloride from diethyl ether. M.p. 63–68° C.

49. (cis)-2-(N-Methylpiperidin-4-yl)-4-(3,4-dimethoxyphenyl)-4a,5,6,7,8,8a-hexahydro-2H-phthalazin-1-one fumarate A mixture of 10 mmol of compound 1, 10 mmol of 4-chloro-N-methylpiperidine hydrochloride and 20 mmol of sodium hydride in dimethylformamide was heated for 150 hours at 120° C. After evaporating the reaction mixture, the residue was purified by chromatography (ethyl acetate: triethylamine/10:1). Crystallized from tetrahydrofuran as the fumarate. M.p. 200° C. (with decomposition)

50. (cis)-4-(3,4-Diethoxyphenyl)-2-(2-nitroxy-1-ethyl)-4a,5,6,7,8,8a-hexahydro-2H-phthalazin-1-one hydrochloride A mixture of 20 mmol of acetic anhydride and 20 mmol of nitric acid was added to a solution of 10 mmol of compound 35 in 100 ml of dichloromethane at 0° C. After 30 min 150 ml of water was added to the mixture and the organic layer dried over magnesium sulfate and evaporated. Crystallisation from ethyl acetate. M.p. 139–140° C.

51. (cis)-N,N-Dimethyl-4-(4-(3,4-dimethoxyphenyl)-1-oxo-4a,5,6,7,8,8a-hexahydro-1H-phthalazin-2-yl)acetamide 5 mmol of ethyl chloroformate was added to a mixture of 5 mmol of compound 38 and 5 mmol of triethylamine in dichloromethane at −20° C. After stirring this mixture for 30 min, a mixture of 6 mmol of dimethylammoniumchloride and 6 mmol of triethylamine in dichloromethane was added and the resulting mixture stirred for 1 hour at room temperature after which aqueous sodium carbonate was added to the reaction mixture. The organic layer was dried over magnesium sulfate and evaporated. Crystallized from ethyl acetate/diethyl ether. M.p. 142–145° C.

52. (cis)-4-(3,4-Dimethoxyphenyl)-2-(2-oxo-2-phenylethyl)-4a,5,6,7,8,8a-hexahydro-2H-phthalazin-1-one Prepared from compound 1 and 2-bromoacetophenone as described for compound 8. Purified by chromatography [ethyl acetate: petroleum ether (60–80° C.)/1:3]. Crystallized from diethyl ether. M.p. 133–135° C.

53. (cis)-4-(3,4-Dimethoxyphenyl)-2-(2-(2-methoxyphenyl)-2-oxoethyl)-4a,5,6,7,8,8a-hexahydro-2H-phthalazin-1-one A mixture of 2 g of compound 1 and 1 eq sodium ethanolate in 30 ml of dimethylformamide was added to a solution of 2 g of ω-bromo-2-methoxyacetophenone in dimethylformamide. After 30 min small portions of additional ω-bromo-2-methoxyacetophenone (total 5 gram) and sodium ethanolate were added during 2 hours. Subsequently the reaction mixture was evaporated and the residue partitioned between water and ethyl acetate. The organic layer was dried over magnesium sulfate and evaporated. The residue was purified by chromatography (dichloromethane). Crystallized from methanol. M.p. 93°–96° C.

54. (cis)-2-(2-(4-Chlorophenyl)-2-oxoethyl)-4-(4,5-dimethoxyphenyl)-4a,5,6,7,8,8a-hexahydro-2H-phthalazin-1-one Prepared from ω-bromo-4-chloroacetophenone and compound 1 as described for compound 8. Crystallized from methanol. M.p. 142°–144° C.

55. (cis)-4-(3,4-Dimethoxyphenyl)-2-(2-(2-naphthyl)-2-oxoethyl)-4a,5,6,7,8,8a-hexahydro-2H-phthalazin-1-one Prepared from compound 1 and α-bromo-2'-acetonaphthone as described for compound 8. Purified by chromatography [ethyl acetate: petroleum ether (60°–80° C.)/1:3]. Crystallized from methanol at −20° C. M.p. 89°–90° C.

56. (cis)-4-(3,4-Dimethoxyphenyl)-2-diphenylmethyl-4a,5,6,7,8,8a-hexahydro-2H-phthalazin-1-one Prepared from compound 1 and diphenylchloromethane as described for compound 8. Purified by chromatography (dichloromethane). Crystallized from methanol. M.p. 133°–135° C.

57. (cis)-4-(3,4-Dimethoxyphenyl)-2-(3-phenoxy-1-propyl)-4a, 5,6,7,8,8a-hexahydro-2H-phthalazin-1-one Prepared from compound 1 and 3-phenoxy-1-bromopropane as described for compound 8. Purified by chromatography (dichloromethane). Crystallized from petroleum ether (60°–80° C.). M.p. 78°–81° C.

58. (cis)-4-(3,4-Dimethoxyphenyl)-2-(4-bromo-1-butyl)-4a,5,6,7,8,8a-hexahydro-2H-phthalazin-1-one 15 g of 1,4-dibromobutane was added to a mixture of 5.0 g of compound 1 and 1.0 g of sodium hydride in dimethylformamide. After stirring the resulting mixture for 5 hours, the solvent was evaporated and the residue partitioned between water and ethyl acetate. The ethyl acetate solution was dried over magnesium sulfate and evaporated. The residue was purified by chromatography (dichloromethane). M.p. colourless oil.

$^1$H-NMR(CDCl$_3$): 1.20–1.97(m,11H,7xcyclohexyl H,Br—C—CH$_2$—CH$_2$);
2.44–2.73(m,2H,2xcyclohexyl H); 2.88–3.15(m,1H, cyclohexyl H);
3.49(t,J=6.0 Hz,2H,Br—CH$_2$); 3.72–4.12(m,8H,N—CH$_2$, 2xO—CH$_3$):
6.84(d,J=8.4 Hz,1H,arom.H); 7.21(dd,J=2.0,8.4 Hz, 1H,arom.H);
7.47(d,J=2.0 Hz,1H, arom.H).

59. (cis)-4-(3,4-Dimethoxyphenyl)-2-phenyl-4a,5,6,7,8,8a-hexahydro-2H-phthalazin-1-one Prepared from compound A (see starting compounds) and phenylhydrazine as described for compound 14. Crystallized from ethyl acetate/petroleum ether (60°–95° C.). M.p. 122°–124° C.

60. (cis)-4-(3,4-Dimethoxyphenyl)-2-phenyl-4a,5,8,8a-tetrahydro-2H-phthalazin-1-one Prepared from compound C (see starting compounds) and phenylhydrazine as described for compound 35. Crystallized from diethyl ether. M.p. 134°–135° C.

61. (cis)-4-(3-Ethoxy-4-methoxyphenyl)-2-phenyl-4a,5,8,8a-tetrahydro-2H-phthalazin-1-one Prepared from compound F (see starting compounds) and phenylhydrazine as described for compound 35. Crystallization from diethyl ether at −20° C. M.p. 97°–99° C.

62. (cis)-4-(3-Cyclopentyloxy-4-methoxyphenyl)-2-phenyl-4a,5,8,8a-tetrahydro-2H-phthalazin-1-one Prepared from compound E (see starting compounds) and phenylhydrazine as described for compound 35. Crystallization from methanol. M.p. 134°–135° C.

63. (cis)-4-(3,4-Dimethoxyphenyl)-2-(2-methylphenyl)-4a,5,8,8a-tetrahydro-2H-phthalazin-1-one Prepared from compound C (see starting compounds) and 2-methylphenylhydrazine as described for compound 35. Crystallization from methanol. M.p. 144°–145° C.

64. (cis)-4-(3,4-Dimethoxyphenyl)-2-(4-tert-butylphenyl)-4a,5,8,8a-tetrahydro-2H-phthalazin-1-one Prepared from 4-tert-butylphenylhydrazine and compound C as described for compound 35. After evaporation of the solvent, the compound was crystallized from ethanol. M.p. 197°–199° C.

65. (cis-4-(3,4-Dimethoxyphenyl)-2-(2-chlorophenyl)-4a,5,8,8a-tetrahydro-2H-phthalazin-1-one Prepared from 4-chlorophenylhydrazine and compound C as described for compound 35. Crystallized from methanol. M.p. 131°–134° C.

66. (cis)-4-(3,4-Dimethoxyphenyl)-2-(4-Chlorophenyl)-4a,5,8,8a-tetrahydro-2H-phthalazin-1-one Prepared from 2-chlorophenylhydrazine and compound C as described for compound 35. M.p. 140°–141° C.

67. (cis)-4-(4-(3,4-Dimethoxyphenyl)-1-oxo-4a,5,8,8a-tetrahydro-1H-phthalazin-2-yl)benzoic acid Prepared from compound C and 4-hydrazinobenzoic acid as described for compound 35. Purified by chromatography and crystallized from ethyl acetate. M.p. 198°–199° C.

68. (cis)-3-(4-(3,4-Dimethoxyphenyl)-1-oxo-4a,5,8,8a-tetrahydro-1H-phthalazin-2-yl)benzoic acid Prepared from compound C and 3-hydrazinobenzoic acid as described for compound 35. Crystallized from ethyl acetate/petroleum ether (60°–80° C.). M.p. 185°–186° C.

69. (cis)-n-Propyl-4-(4-(3,4-dimethoxyphenyl)-1-oxo-4a,5,8,8a-tetrahydro-1H-phthalazin-2-yl)benzoate A solution of 1 g of compound 67 and 1 g of p-toluenesulfonic acid in 100 ml of 1-propanol was refluxed for 18 h. After evaporating the solvent, the title compound was crystallized from methanol. M.p. 100°–101° C.

70. (cis)-4-(3,4-Dimethoxyphenyl)-2-(4-(2-hydroxyethyl)phenyl)-4a,5,8,8a-tetrahydro-2H-phthalazin-1-one Prepared from compound C and 2-(4-hydrazinophenyl)ethanol as described for compound 35. Crystallized from diethyl ether. M.p. 137°–139° C.

71. (cis)-4-(4-(3,4-Dimethoxyphenyl)-1-oxo-4a,5,8,8a-tetrahydro-1H-phthalazin-2yl)phenylacetic acid Prepared from compound C and 4-hydrazinophenylacetic acid as described for compound 35. Crystallized from diethyl ether. M.p. 162° C.

72. (cis)-4-(3,4-Dimethoxyphenyl)-2-(4-nitrophenyl)-4a,5,8,8a-tetrahydro-2H-phthalazin-1-one Prepared from compound C and 4-nitrophenylhydrazine as described for compound 35. Crystallized from methanol. M.p. 179°–182° C.

73. (cis)-4-(3,4-Dimethoxyphenyl)-2-(4-aminosulfonylphenyl)-4a,5,8,8a-tetrahydro-2H-phthalazin-1-one Prepared from 2 g of 4-sulfonamidophenylhydrazine and 3 g of compound C as described for compound 35. After evaporating the solvent, the residue was crystallized from methanol and recrystallized from tetrahydrofuran/petroleum ether (60°–80° C.). M.p. 181°–183° C.

74. (cis)-4-(3,4-Dimethoxyphenyl)-2-(4-aminophenyl-4a,5,8,8a-tetrahydro-2-phthalazin-1-one A mixture of 35 mmol of compound 72 and 15 g of iron in a mixture of 300 ml of ethanol and 80 ml of water at 65° C. was treated with 10 ml of 2N hydrochloric acid during 45 min. After filtering, the solvent was evaporated and the residue washed with ethyl acetate. M.p. 183°–185° C.

75. (cis)-4-(3,4-Dimethoxyphenyl)-2-(4-(4-methylphenylsulfonamido)phenyl)-4a,5,8,8a-tetrahydro-2H-phthalazin-1-one 20 mmol of p-toluenesulfonyl chloride was added to a solution of 10 mmol of compound 74 in 100 ml of pyridine and the resulting mixture was left over night at room temperature. After evaporating the solvent, the residue was partioned between aqueous sodium carbonate and ethyl acetate. The organic layer was dried over magnesium sulfate and evaporated. Crystallisation from methanol. M.p. 229°–230° C.

76. (cis)-5-[4-(4-(3,4-Dimethoxyphenyl)-1-oxo-4a,5,8,8a-tetrahydrophthalazin-2yl)phenyl]-2-ethyletrazole Prepared from compound C and 4-(2-ethyltetrazol-5yl)phenylhydrazine as described for compound 35. Crystallized from diethyl ether. M.p. 135°–137° C.

77. (cis)-5-[4-(4-(3,4-Dimethoxyphenyl)-1-oxo-4a,5,8,8a-tetrahydrophthalazin-2yl)phenyl]-2-benzyltetrazole Prepared from compound C (see starting compounds) and compound N (see starting compounds) as described for compound 35. Crystallized from methanol. M.p. 100°–102° C.

78. (cis)-2-Benzyl-4-(3,4-dimethoxyphenyl)-4a,5,6,7,8,8a-hexahydro-2H-phthalazin-1-one 6 mmol of a 60% suspension of sodium hydride in mineral oil was added to a suspension of 5 mmol of compound 1 in about 40 ml of dimethylformamide, under a flow of nitrogen at room temperature. After stirring this mixture for 30 minutes, 7 mmol of benzylchloride was added and the resulting mixture was stirred for another 4 hours, after which the solvent was evaporated. The residue was partitioned between ethyl acetate and water, the organic layer was dried over magnesium sulfate and evaporated. The residue was crystallized from methanol. M.p. 117°–118° C.

79. (trans)-2-Benzyl-4-(3,4-dimethoxyphenyl)-4a,5,6,7,8, 8a-hexahydro-2-H-phthalazin-1-one A mixture of 10 mmol of compound B (see starting compounds) and 10 mmol of benzylhydrazine hydrochloride in 100 ml of toluene was refluxed for 8 hours in a Dean Stark apparatus. After cooling to room temperature, the mixture was washed with aqueous sodium carbonate, dried over magnesium sulfate and evaporated. The residue was purified by column chromatography [ethyl acetate: petroleum ether (60°–80° C.)/1:3] and the compound crystallized from diethyl ether. M.p. 86°–88° C.

80. (cis)-2-Benzyl-4-(3,4-dimethoxyphenyl)-4a,5,8,8a-tetrahydro-2H-phthalazin-1-one Prepared from compound 3 and benzylchloride as described for compound 78. Purified by chromatography [ethyl acetate: petroleum ether (60°–80° C.)/1:3]. Crystallized from diethyl ether. M.p. 133°–135° C.

81. (cis)-2-Benzyl-4-(3-cyclopentyloxy-4-methoxyphenyl)-4a,5,6,7,8,8a-hexahydro-2H-phthalazin-1-one Prepared from compound 4 and benzylchloride as described for compound 78. Purified by chromatography [petroleum ether (60°–95° C.): ethyl acetate/4:1] and crystallized from petroleum ether (60°–95° C.)/ethyl acetate. M.p. 91°–92° C.

82. (cis)-2-Benzyl-4-(3,4-diethoxyphenyl)-4a,5,6,7,8,8a-hexahydro-2H-phthalazin-1-one Prepared from compound 7 and benzylchloride as described for compound 78. Crystallized from petroleum ether (60°–95° C.). M.p. 91°–92° C.

83. (cis)-4-(4-(3,4-Dimethoxyphenyl)-1-oxo-4a,5,6,7,8,8a-hexahydro-1H-phthalazin-2-ylmethyl)-benzoic acid Prepared from compound 1 and 4-chloromethylbenzoic acid as described for compound 78 using 12 mmol of sodium hydride instead of 6 mmol. After evaporating the reaction mixture, the residue was partitioned between aqueous sodium carbonate and ethyl acetate. The aqueous solution was acidified with hydrochloric acid and extracted with ethyl acetate. The organic layer was dried over magnesium sulfate and evaporated. The compound was purified by chromatography (ethyl acetate) and crystallized from diethyl ether. M.p. 135°–139° C.

84. (cis)-4-(4-(3-Ethoxy-4-methoxyphenyl)-1-oxo-4a,5,8, 8a-tetrahydro-1H-phthalazin-2-ylmethyl)benzoic acid hemietherate Prepared from compound 6 and 4-chloromethylbenzoic acid as described for compound 83. Crystallized from diethyl ether/petroleum ether (60°–80° C.). M.p. 132°–133° C.

85. (cis)-4-(4-(3,4-Diethoxyphenyl)-1-oxo-4a,5,6,7,8,8a-hexahydro-1H-phthalazin-2-yl-methyl)benzoic acid Prepared from compound 7 and 4-chloromethylbenzoic acid as described for compound 83. Purified by chromatography (dichloromethane). Crystallized from diethyl ether. M.p. 152°–154° C.

86. (cis)-4-(4-(3-Cyclopentyloxy-4-methoxyphenyl)-1-oxo-4a,5,6,7,8,8a-hexahydro-1H-phthalazin-2-ylmethyl)benzoic acid Prepared from compound 4 and 4-chloromethylbenzoic acid as described for compound 83. Crystallized from ethyl acetate. M.p. 189°–190° C.

87. (cis)-4-(4-(3,4-Dimethoxyphenyl)-1-oxo-4a,5,8,8a-tetrahydro-1H-phthalazin-2-yl-methyl)benzoic acid Prepared from compound 3 and 4-chloromethylbenzoic acid as described for compound 83. Crystallized from ethyl acetate. M.p. 192°–193° C.

88. (cis)-3-(4-(3,4-Dimethoxyphenyl)-1-oxo-4a,5,6,7,8,8a-hexahydro-1H-phthalazin-2-ylmethyl)benzoic acid Prepared from compound 1 and 3-bromomethylbenzoic acid as described for compound 83. Purified by chromatography (ethyl acetate). Crystallized from diethyl ether. M.p. 133°–136° C.

89. (cis)-4-(4-(3,4-Dimethoxyphenyl)-1-oxo-4a,5,6,7,8,8a-hexahydro-1H-phthalazin-2-ylmethyl)phenylacetic acid Prepared from compound 1 and 4-chloromethylphenylacetic acid as described for compound 83. Purified by chromatography (ethyl acetate). Crystallized from diethyl ether. M.p. 164°–166° C.

90. (cis)-4-(3,4-Dimethoxyphenyl)-2-(2-methoxybenzyl)-4a,5,6,7,8,8a-hexahydro-2H-phthalazin-1-one Prepared from compound 1 and 2-methoxybenzylchloride as described for compound 78. Purified by chromatography (dichloromethane). Crystallized from diethyl ether at −20° C. M.p. 96°–99° C.

91. (cis)-4-(3,4-Dimethoxyphenyl)-2-(3-methoxybenzyl)-4a,5,6,7,8,8a-hexahydro-2H-phthalazin-1-one Prepared from compound 1 and 3-methoxybenzylchloride as described for compound 78. Crystallized from methanol. M.p. 115° C.

92. (cis)-4-(3,4-Dimethoxyphenyl)-2-(4-methoxybenzyl)-4a,5,6,7,8,8a-hexahydro-2H-phthalazin-1-one Prepared from compound 1 and 4-methoxybenzylchloride as described for compound 78. Crystallized from diethyl ether. M.p. 77°–78° C.

93. (cis)-4-(3,4-Dimethoxyphenyl)-2-(3,5-dimethoxybenzyl)-4a,5,6,7,8,8a-hexahydro-2H-phthalazin-1-one Prepared from compound 1 and 3,5-dimethoxybenzylchloride as described for compound 78. Purified by chromatography (dichloromethane). Crystallized from methanol. M.p. 114°–117° C.

94. (cis)-4-(3,4-Dimethoxyphenyl)-2-(2-trifluoromethylbenzyl)-4a,5,6,7,8,8a-hexahydro-2H-phthalazin-1-one Prepared from compound 1 and 2-trifluoromethylbenzylchloride as described for compound 78. Purified by chromatography (dichloromethane). Crystallized from petroleum ether (60°–95° C.). M.p. 87°–88° C.

95. (cis)-2-(2-Chlorobenzyl)-4-(3,4-dimethoxyphenyl)-4a, 5,6,7,8,8a-hexahydro-2H-phthalazin-1-one Prepared from compound 1 and 2-chlorobenzylchloride as described for compound 78. Purified by chromatography (dichloromethane). Crystallized from petroleum ether (60°–95° C.). M.p. 101°–104° C.

96. (cis)-4-(3,4-Dimethoxyphenyl)-2-(4-hydroxybenzyl)-4a,5,6,7,8,8a-hexahydro-2H-phthalazin-1-one Prepared from compound 122 by catalytic debenzylation in ethanol using 5% Palladium on carbon. Crystallized from diethyl ether. M.p. 177°–179° C.

97. (cis)-4-(3,4-Dimethoxyphenyl)-2-(2-hydroxybenzyl)-4a,5,6,7,8,8a-hexahydro-2H-phthalazin-1-one Prepared from compound 126 by catalytic debenzylation as described for compound 96. M.p. 132°–133° C.

98. Methyl (cis)-4-(4-(3,4-dimethoxyphenyl)-1-oxo-4a,5,6, 7,8,8a-hexahydro-1H-phthalazin-2-ylmethyl)benzoate 3 ml of thionyl chloride was added slowly to a solution of 1 g of compound 83 in methanol at −20° C. After complete addition, the mixture was stirred for 6 hours at room temperature and subsequently evaporated. The compound was crystallized from diethyl ether at −20° C. M.p. 90°–92° C.

99. (cis)-4-(3,4-Dimethoxyphenyl)-2-(2-pyridyl)-4a,5,8,8a-tetrahydro-2H-phthalazin-1-one Prepared from compound C and 2-pyridylhydrazine as described for compound 35. Purified by chromatography (ethyl acetate) and crystallized from ethyl acetate/diethyl ether. M.p. 147°–148° C.

100. (cis)-4-(3,4-Dimethoxyphenyl)-2-(2-pyridylmethyl)-4a,5,6,7,8,8a-hexahydro-2H-phthalazin-1-one Prepared from compound 1 and 2-picolylchloride hydrochloride as described for compound 105. Crystallized from diethyl ether. M.p. 181°–182° C.

101. (cis)-4-(3,4-Dimethoxyphenyl)-2-(2-pyridylmethyl)-4a,5,8,8a-tetrahydro-2H-phthalazin-1-one Prepared from compound 3 and 2-picolylchloride hydrochloride as described for compound 105. Crystallized from diethyl ether. M.p. 146°–147° C.

102. (cis)-4-(3,4-Dimethoxyphenyl)-2-(3-pyridylmethyl)-4a,5,6,7,8,8a-hexahydro-2H-phthalazin-1-one hydrochloride Prepared from compound 1 and 3-picolylchloride hydrochloride as described for compound 105. Purified by chromatography (dichloromethane). Crystallized from diethyl ether as the hydrochloride. M.p. 192°–195° C.

103. (cis)-4-(3,4-Dimethoxyphenyl)-2-(3-pyridylmethyl)-4a,5,8,8a-tetrahydro-2H-phthalazin-1-one Prepared from compound 3 and 3-picolylchloride hydrochloride as described for compound 105. Purified by chromatography (ethyl acetate). Crystallized from diethyl ether. M.p. 117°–120° C.

104. (cis)-4-(3,4-Dimethoxyphenyl)-2-(4-pyridylmethyl)-4a,5,8,8a-tetrahydro-2H-phthalazin-1-one Prepared from compound 3 and 4-picolylchloride hydrochloride as described for compound 105. Purified by chromatography (ethyl acetate). Crystallized from diethyl ether. M.p. 121°–124° C.

105. (cis)-4-(3,4-Dimethoxyphenyl)-2-(4-pyridylmethyl)-4a,5,6,7,8,8a-hexahydro-2H-phthalazin-1-one Prepared from compound 1 and 4-picolylchloride hydrochloride as described for compound 78, using 12 mmol of sodium hydride instead of 6 mmol. Purified by chromatography (dichloromethane). Crystallized from diethyl ether. M.p. 87°–89° C.

106. (cis)-4-(3,4-Dimethoxyphenyl)-2-(2-indanyl)-4a,5,8,8a-tetrahydro-2H-phthalazin-1-one Prepared from compound C and 2-indanylhydrazine hydrochloride as described for compound 35. Crystallized from methanol (2x). M.p. 163°–164° C.

107. (cis)-4-(3,4-Dimethoxyphenyl)-2-(1,4-benzodiazin-2yl)-4a,5,8,8a-tetrahydro-2H-phthalazin-1-one Prepared from compound C and 2-hydrazino-1,4-benzodiazine as described for compound 35. Purified by chromatography and crystallized from diethyl ether. M.p. 154°–156° C.

108. (cis)-4-(3,4-Dimethoxyphenyl)-2-(2-benzothiazolyl)-4a,5,8,8a-tetrahydro-2H-phthalazin-1-one Prepared from compound C and 2-hydrazinobenzothiazole as described for compound 35. Crystallized from ethyl acetate/petroleum ether (60°–80° C). M.p. 176°–177° C.

109. (cis)-4-(3,4-Dimethoxyphenyl)-2-(2-methylthiazole-4-yl)-4a,5,6,7,8,8a-hexahydro-2H-phthalazin-1-one Prepared from compound 1 and 4-chloromethyl-2-methylthiazole as described for compound 78. Crystallized from ethyl acetate. M.p. 135°–137° C.

110. (cis)-2-(Benzotriazol-1-ylmethyl)-4-(3,4-dimethoxyphenyl)-4a,5,6,7,8,8a-hexahydro-2H-phthalazin-1-one Prepared from compound 1 and 1-bromoethylbenzotriazole as described for compound 78, using sodium ethanolate instead of sodium hydride. Purified by chromatography [ethyl acetate:petroleum ether (60°–95° C.)/1:2]. Crystallized from methanol. M.p. 173°–178° C.

111. (cis)-4-(3,4-Dimethoxyphenyl)-2-(2-phenylethyl)-4a,5,6,7,8,8a-hexahydro-2H-phthalazin-1-one Prepared from 2-bromoethylbenzene and compound 1 as described for compound 78. Purified by chromatography [ethyl acetate: petroleum ether (60°–80° C.)/1:3]. Crystallized from methanol. M.p. 99°–100° C.

112. (cis)-4-(3,4-Dimethoxyphenyl)-2-(2-bromoethyl)-4a,5,6,7,8,8a-hexahydro-2H-phthalazin-1-one hydrochloride A solution of 25 mmol of bromine in 10 ml of dichloromethane was added to a solution of 25 mmol of triphenylphosphine in 50 ml of dichloromethane at 0° C. under a flow of nitrogen, followed by the addition of 25 mmol of compound 35 in 25 ml of dichloromethane. After complete addition, the mixture was stirred for 2 h at room temperature. The reaction mixture was washed with aqueous sodium carbonate, dried over magnesium sulfate and evaporated. The compound was crystallized from methanol. M.p. 134°–136° C.

113. (cis)-4-(3,4-Dimethoxyphenyl)-2-(2-(1-imidazolyl)ethyl)-4a,5,6,7,8,8a-hexahydro-2H-phthalazin-1-one hydrochloride A solution of 2 g of compound 112 and 3 g of imidazole in methanol was left for 18 h at room temperature. After evaporating the solvent, the residue was partitioned between water and ethyl acetate. The organic layer was dried over magnesium sulfate and evaporated. The residue was dissolved in ethyl acetate and filtered over silica. The compound crystallized as the hydrochloride from tetrahydrofuran. M.p. 198°–199° C.

114. (cis)-4-(3,4-Dimethoxyphenyl)-2-(4-bromo-1-butyl)-4a,5,8,8a-tetrahydro-2H-phthalazin-1-one Prepared from compound C and 1,4-dibromobutane as described for compound 58. M.p. 105°–106° C.

115. (cis)-4-(3,4-Dimethoxyphenyl)-2-(4-(1-imidazolyl)-1-butyl)-4a,5,6,7,8,8a-hexahydro-2H-phthalazin-1-one hydrochloride Prepared from compound 58 as described for compound 113. M.p. 210°–212° C.

116. (cis)-4-(3,4-Dimethoxyphenyl)-2-(4-(1-imidazolyl)-1-butyl)-4a,5,8,8a-tetrahydro-2H-phthalazin-1-one hydrochloride Prepared from compound 114 and imidazole as described for compound 113. The reaction mixture was evaporated and the residue dissolved in 2N HCl. After extraction with dichloromethane and drying over magnesium sulfate, the solvent was evaporated. The residue crystallized on treating with ethyl acetate. M.p. 192°–194° C.

117. (cis)-4-(3,4-Dimethoxyphenyl)-2-(6-bromo-1-hexyl)-4a,5,8,8a-tetrahydro-2H-phthalazin-1-one Prepared from compound C and 1,6-dibromohexane as described for compound 58. M.p. 55°–56° C.

118. (cis)-4-(3,4-Dimethoxyphenyl)-2-(6-(1-imidazolyl)-1-hexyl)-4a,5,8,8a-tetrahydro-2H-phthalazin-1-one hydrochloride Prepared from compound 117 and imidazole as described for compound 113. Purified by chromatography and crystallized as the hydrochloride from tetrahydrofurane. M.p. 183° C.

119. (cis)-2-(6-(2-Benzimidazole)-1-hexyl)-4-(3,4-dimethoxyphenyl)-4a,5,8,8a-tetrahydro-2H-phthalazin-1-one hydrochloride Prepared from compound 117 and benzimidazole as described for compound 113. Purified by chromatography (ethyl acetate) and crystallized as the hydrochloride. M.p. 67°–70° C.

120. (cis)-N-[6-(4-(3,4-Dimethoxyphenyl)-1-oxo-4a,5,8,8a-tetrahydrophthalazin-2-yl)hexyl]-phthalamide A mixture of 10 g of compound 117, 10 g of phthalimide and 10 g of potassium carbonate was heated for 5 h at 100° C. in DMF. The mixture was diluted with water and extracted with ethyl acetate. The organic layer was dried over magnesium sulfate and evaporated. The residue was purified by chromatography (dichloromethane) and crystallized from ethyl acetate/ether. M.p. 104°–105° C.

121. (cis)-4-(3,4-Dimethoxyphenyl)-2-(3-phenyl-2-[trans]propenyl)-4a,5,6,7,8,8a-hexahydro-2H-phthalazin-1-one Prepared from compound 1 and 3-phenyl-2-[trans]propenylchloride as described for compound 78. Purified by chromatography (dichloromethane). Crystallized from diethyl ether at −20° C. M.p. 76°–79° C.

122. (cis)-4-(3,4-Dimethoxyphenyl)-2-(4-benzyloxybenzyl)-4a,5,6,7,8,8a-hexahydro-2H-phthalazin-1-one Prepared from compound 1 and 4-benzyloxybenzylchloride as described from compound 78. Purified by chromatography (dichloromethane) and isolated as a colourless oil.

$^1$H/NMR(CDCl$_3$): 1.26–1.86 (m, 7 H, 7 x cyclohexyl H); 2.47–2.76 (m, 2 H, 2 x cyclohexyl H); 3.00–3.16 (m, 1 H, cyclohexyl H); 3.93 (s, 6 H, 2 x O—CH$_3$); 4.83–5.15 (m, 4 H, N—CH$_2$, O—CH$_2$); 6.80–6.97 (m, 3 H, arom. H); 7.15–7.47 (m, 9 H, arom. H).

123. (cis)-2-[6-(4-(3,4-Dimethoxyphenyl)-1-oxo-4a,5,8,8a-tetrahydrophthalazin-2yl)hexyloxy]-benzoic acid sodium salt A mixture of 4 g of compound 114, 3 g of ethyl salicylate and 3 g of potassium carbonate in 100 ml of DMF was heated for 2 h at 100° C. After evaporating the reaction mixture, the residue was partitioned between aqueous sodium carbonate and ethyl acetate. The organic solvent was evaporated and the residue dissolved in a mixture of 100 ml of methanol, 100 ml of tetrahydrofuran and 200 ml of 2N potassium hydroxide. The mixture was heated for 2 h at 60°C. and subsequently evaporated. After extraction with ethyl acetate the compound was purified by chromatography and precipitated from ether with a concentrated solution of sodium ethanolate in ethanol. Crystallisation from tetrahydrofuran/diethyl ether. M.p. 141°–144° C.

124. (cis)-4-(3,4-Dimethoxyphenyl)-2-(tetrahydropyran-4-yl)-4a,5,8,8a-tetrahydro-2H-phthalazin-1-one Prepared from compound C and 4-hydrazinotetrahydropyran as described for compound 35. Crystallized from methanol. M.p. 175°–177° C.

125. (cis)-4-(3,4-Dimethoxyphenyl)-2-(tetrahydrothiopyran-4-yl)-4a,5,8,8a-tetrahydro-2H-phthalazin-1-one Prepared from compound C and 4-hydrazinotetrahydrothiopyran as described for compound 35. Crystallized from methanol. M.p. 140°–141° C.

126. (cis)-4-(3,4-Dimethoxyphenyl)-2-(2-benzyloxybenzyl)-4a,5,6,7,8,8a-hexahydro-2H-phthalazin-1-one Prepared from compound 1 and 2-benzyloxybenzylchloride as described for component 78. Purified by chromatography [ethyl acetate/petroleum ether (60°–80° C.), 1:3]. M.p. colourless oil.

$^1$H-NMR(CDCl$_3$): 1.22–1.83 (m, 7 H, 7 x cyclohexyl H), 2.41–2.73 (m, 2 H, 2 x cyclohexyl H), 3.00–3.16 (m, 1 H, cyclohexyl H), 3.91 (s, 3 H, O—CH$_3$), 3.93 (s, 3 H, O—CH$_3$), 4.83–5.16 (m, 4 H, N—CH$_2$, O—CH$_2$), 6.80–6.97 (m, 3 H, Ar—H), 7.15–7.48 (m, 9 H, Ar—H).

Starting compounds

A. 2-(3,4-Dimethoxybenzoyl)[cis]cyclohexanecarboxylic acid 0.5 mole of 1,2-dimethoxybenzene was added slowly to a suspension of 0.5 mole aluminiumtrichloride in 1 l of dichloromethane at 0° C. After complete addition, cis-cyclohexane-1,2-dicarboxylic anhydride was added to the solution. After 8 hours of reflux the solution was poured onto ice. The organic layer was dried over magnesium sulfate and evaporated. The residue was washed with diethyl ether and dried. M.p. 171°–175° C.

B. 2-(3,4-Dimethoxybenzoyl)[trans]cyclohexanecarboxylic acid

Prepared from trans-cyclohexane-1,2-dicarboxylic anhydride and 1,2-dimethoxybenzene as described for compound A M.p. 202°–205° C.

C. (cis)-2-(3,4-Dimethoxybenzoyl)-1,2,3,6-tetrahydrobenzoic acid

Prepared from 1,2-dimethoxybenzene and cis-1,2,3,6-tetrahydrophthalic anhydride as described for compound A. M.p. 110°–112° C.

D. 2-(3-Cyclopentoxy-4-methoxybenzoyl)-cis-cyclohexanecarboxylic acid

4-Bromo-2-cyclopentyloxy-1-methoxybenzene (16.3 g, 60 mmol) was dissolved in THF (200 ml) and cooled with an ethanol/N$_2$ bath to −90° C. BuLi (41 ml, 66 mmol) was added dropwise while keeping the temperature below −80° C. and stirred for another 15 min after the last addition. This mixture was then quickly added under a nitrogen atmosphere to a cooled solution (−90° C.) of cis-1,2-cyclohexanedicarboxylic anhydride (11.1 g, 72 mmol) in THF (200 ml). After stirring for 2 h at −80° C. solid ammoniumchloride was added and the reaction mixture was allowed to warm slowly to room temperature. Water (300 ml) was added and the anorganic layer was washed with ethyl acetate (200 ml). The combined organic extracts were washed with water (300 ml) and brine (2×300 ml), dried (MgSO$_4$) and the solvent removed under reduced pressure. The residue was dissolved in dichloromethane and purified by chromatography (petroleum ether (60°–95° C.)/ethyl acetate: 7/13) and crystallized from petroleum ether (60°–95° C.)/ethyl acetate to give the title compound (10.1 g) as a white solid. M.p. 120°–121° C.

E. (cis)-2-(3-Cyclopentyloxy-4-methoxybenzoyl)-1,2,3,6-tetrahydrobenzoic acid

A solution of 100 mmol of 1-Bromo-3-cyclopentyloxy-4-methoxybenzene in tetrahydrofuran was added slowly to a mixture of 1.1 equivalent of magnesium. After complete addition, the mixture was refluxed for 5 h and left at room temperature for additional 18 h. The mixture was added slowly to a solution of (cis)-1,2,3,6-tetrahydrophthalic anhydride in tetrahydrofuran at 0° C. After complete addition the mixture was refluxed for 6 h and left at room temperature for addition 18 h after which the reaction was quenched with ammonium chloride and the solvent removed under reduced pressure. The residue was acidified with concentrated hydrochloric acid and the mixture extracted with diethyl ether. The organic layer was dried over magnesium sulfate and evaporated. The residue was dissolved in dichloromethane and the solution filtered over silica. After evaporating this dichloromethane solution, the compound was crystallized from diethyl ether. M.p. 114–115° C.

F. (cis)-2-(3-Ethoxy-4-methoxybenzoyl)-1,2,3,6-tetrahydrobenzoic Acid

Prepared from 1-Bromo-3-ethoxy-4-methoxybenzene and tetrahydrophthalic anhydride as described for compound D. M.p. 132–135° C.

G. 2-(3,4-Diethoxybenzoyl)[cis]cyclohexanecarboxylic Acid

Prepared from 1,2-diethoxybenzene and cis-hexahydrophthalic anhydride as described for compound A. M.p.: low melting solid.

$^1$H-NMR(CDCl$_3$): 1.28–2.27(m, 14H, 8 cyclohexane H, 2×C—CH$_3$); 2.66(quintet, J=4.8 Hz, 1H, cyclohexane H); 3.91–3.97(m, 1H, C—CH(C)—C); 4.01–4.25(m, 4H, 2×O—CH$_2$); 6.89(d, J=8.2 Hz, 1H, arom. H); 7.48–7.53 (m, 2H, arom. H)

H. (cis)-4-(4-Methoxy-3-hydroxyphenyl)-2-cyclopentyl-4a,5,8,8a-tetrahydro-2H-phthalazin-1one A solution of 3.3 g of compound 21 and 2 g of p-toluenesulfonic acid in 15 ml of toluene was refluxed for 4 h. After cooling to room temperature, themixture was washed with aqueous sodium carbonate, the toluene solution was dried over magnesium sulfate and evaporated. Crystallization from diethyl ether/petroleum ether (60–80° C.). M.p. 142–144° C.

I. (cis)-4-(4-Methoxy-3-hydroxyphenyl)-2-cycloheptyl-4a,5,8,8a-tetrahydro-2H-phthalazin-1one Prepared from compound 26 as described for compound H. M.p. 171° C.

K. 5-(3-Nitrophenyl)tetrazole

A mixture of 14.8 g of 4-nitrobenzonitril, 32 g of ammoniumchloride and 39 g of sodium azide in 150 ml of DMF was heated for 2 h at 120° C. After evaporating the solvent, the residue was partitioned between 2N hydrochloric acid and ethyl acetate. The organic layer was dried and evaporated. The residue was washed with ether and dried. M.p. 101–102° C.

L. 2-Benzyl-5-(4-nitrophenyl)tetrazole

A mixture of 12 g of compound K, 20 g of potassium carbonate and 12 g of benzylchloride in 100 ml of DMF was heated for 3 h at 100° C. After evaporating the solvent, the residue was partitioned between water and ethyl acetate. The organic layer was dried over magnesium sulfate and evaporated. The residue was washed with diethyl ether and dried. M.p. 139–141° C.

M. 2-Benzyl-5-(4-aminophenyl)tetrazole

Prepared from compound L as described for compound 74. After evaporating the solvent, the residue was dissolved in ethyl acetate and this solution was washed with water, dried over magnesium sulfate and concentrated under reduced pressure. The concentrated solution was filtered over silica and evaporated. The residue was washed with diethyl ether and dried. M.p. 130–132° C.

N. 2-Benzyl-5-(4-hydrazinophenyl)tetrazole

A solution of 1.9 g of sodium nitrite in 10 ml of concentrated hydrochloric acid was slowly added to a solution of 6.5 g of compound M in 20 ml of 2N hydrochloric acid. This was followed by the addition of 17 g of tindichloride dihydrate in 20 ml of water at 0° C. After 30 min the precipitate was filtered off, washed thoroughly with brine and dried. M.p. 182–185° C.

O. 2-Ethyl-5-(4hydrazinophenyl)tetrazole

A mixture of 35 mmol of 2-Ethyl-5-(4-nitrophenyl) tetrazole (prepared analogously to compound L) and 15 g of iron in a mixture of 300 ml of ethanol and 80 ml of water at 65° C., was treated with 10 ml of 2N hydrochloric acid during 45 min. After filtering, the solvent was evaporated. The residue was washed with ethyl acetate and used without further purification in the next step. A solution of 2.2 g of sodium nitrite in 10 ml of conc. hydrochloric acid was slowly added to a solution of the residue mentioned above (2-ethyl-5-(4-aminophenyl)tetrazole) in 20 ml of 2N hydrochloric acid. This was followed by the addition of 22 g of tindichloride dihydrate in 25 ml of water at 0° C. After 30 min. the mixture was extracted with tetrahydrofuran and the organic solution was washed once with a solution of sodium carbonate saturated with sodium chloride. The organic solution was dried over potassium carbonate and evaporated. The residue was used without purification in the next step.

Commercial Utility

The compounds according to the invention have useful pharmacological properties which make then industrially utilizable. As selective cyclic nucleotide phosphodiesterase (PDE) inhibitors (specifically of type 4), they are suitable on the one hand as bronchial therapeutics (for the treatment of airway obstructions on account of their dilating action but also on account of their respiratory rate- or respiratory drive-increasing action) and for the removal of erectile dysfunction on account of their vascular dilating action, but on the other hand especially for the treatment of disorders, in particular of an inflammatory nature, e.g. of the airways (asthma prophylaxis), of the skin, of the intestine, of the eyes, of the CNS and of the joints, which are mediate by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases. In this context, the compounds according to the invention are distinguished by a low toxicity, a good enteral absorption (high bioavailability), a large therapeutic breadth and the absence of significant side effects.

On account of their PDE-inhibiting properties, the compounds according to the invention can be employed in human and veterinary medicine as therapeutics, where they can be used, for example, for the treatment and prophylaxis of the following illnesses: acute and chronic (in particular inflammatory and allergen-induced) airway disorders of varying origin (bronchitis, allergic bronchitis, bronchial asthma); dermatoses (especially of proliferative, inflammatory and allergic type) such as psoriasis (vulgaris), toxic and allergic contact eczema, atopic eczema, seborrhoeic eczema, Lichen simplex, sunburn, pruritus in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on an excessive release of TNF and leukotrienes, for example disorders of the arthritis type (rheumatoid arthritis, rheumatoid spondylitis, osteoarthritis and other arthritic conditions), disorders of the immune system (AIDS, multiple sclerosis), types of shock (septic shock, endotoxin shock, gram-negative sepsis, toxic shock syndrome and ARDS (adult respiratory distress syndrome)) and also generalized inflammations in the gastrointestinal region (Crohn's disease and ulcerative colitis); disorders which are based on allergic and/or chronic, immunological false reactions in the region of the upper airways (pharynx, nose) and the adjacent regions (paranasal sinuses, eyes), such as allergic rhinitis/sinusitis, chronic rhinitis/sinusitis, allergic conjunctivitis and also nasal polyps; but also disorders of the heart which can be treated by PDE inhibitors, such as cardiac insufficiency, or disorders which can be treated on account of the tissue-relaxant action of the PDE inhibitors, such as, for example, erectile dysfunction or colics of the kidneys and of the ureters in connection with kidney stones; and also illnesses of the central nervous system, such as depressions or arteriosclerotic dementia.

The invention further relates to a method for the treatment of mammals, including humans, which are suffering from one of the abovementioned illnesses. The method is characterized in that a therapeutically active and pharmacologically effective and tolerable amount of one or more of the compounds according to the invention is administered to the ill mammal.

The invention further relates to the compounds according to the invention for use in the treatment and/or prophylaxis of illnesses, in particular the abovementioned illnesses.

The invention also relates to the use of the compounds according to the invention for the production of medicaments which are employed for the treatment and/or prophylaxis of the illnesses mentioned.

The invention furthermore relates to medicaments for the treatment and/or prophylaxis of the illnesses mentioned, which contain one or more of the compounds according to the invention.

The medicaments are prepared by processes which are known per se and familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar with auxiliaries which are suitable for the desired pharmaceutical formulations on account of his expert knowledge. In addition to solvents, gel formers, ointment bases and other active compound excipients, for example antioxidants, dispersants, emulsifiers, preservatives, solubilizers or permeation promoters, can be used.

For the treatment of disorders of the respiratory tract, the compounds according to the invention are preferably also administered by inhalation. To do this, these are either administered directly as a powder (preferably in micronized form) or by atomizing solutions or suspensions which contain them. With respect to the preparations and administration forms, reference is made, for example, to the details in European Patent 163 965.

For the treatment of dermatoses, the compounds according to the invention are in particular administered in the form of those medicaments which are suitable for topical application. For the production of the medicaments, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The medicaments according to the invention are prepared by processes known per se. The dosage of the active compounds is carried out in the order of magnitude customary for PDE inhibitors. Topical application forms (such as ointments) for the treatment of dermatoses thus contain the active compounds in a concentration of, for example, 0.1–99%. The dose for administration by inhalation is customarily between 0.1 and 3 mg per day. The customary dose in the case of systemic therapy (p.o. or i.v.) is between 0.03 and 3 mg/kg.

Biological Investigations

In the investigation of PDE 4 inhibition on the cellular plane, the activation of inflammatory cells is ascribed particular importance. An example is FMLP (N-formyl-methionyl-leucyl-phenylalanine)-induced superoxide production of neutrophilic granulocytes, which can be measured as luminol-amplified chemiluminescence. (Mc Phail L C, Strum S L, Leone P A and Sozzani S, The neutrophil respiratory burst mechanism. In "Immunology Series" 57: 47–76, 1992; ed. Coffey R G (Marcel Decker, Inc., New York-Basel-Hong Kong)).

Substances which inhibit chemiluminescence and cytokine secretion and the secretion of proinflammatory mediators in inflammatory cells, in particular neutrophilic and eosinophilic granulocytes, T-lymphocytes, monocytes and macrophages are those which inhibit PDE 4. This isoenzyme of the phosphodiesterase families is particularly represented in granulocytes. Its inhibition leads to an increase in the intracelluar cyclic AMP concentration and thus to the inhibition of cellular activation. PDE 4 inhibition by the substances according to the invention is thus a central indicator for the suppression of inflammatory processes. (Giembycz M A, Could isoenzyme-selective phosphodiesterase inhibitors render bronchodilatory therapy redundant in the treatment of bronchial asthma?. Biochem Pharmacol 43: 2041–2051, 1992; Torphy T J et al., Phosphodiesterase inhibitors: new opportunities for treatment of asthma. Thorax 46: 512–523, 1991; Schudt C et al., Zardaverine: a cyclic AMP PDE 3/4 inhibitor. In "New Drugs for Asthma Therapy", 379–402, Birkhäuser Verlag Basel 1991; Schudt C et al., Influence of selective phosphodiesterase inhibitors on human neutrophil functions and levels of cAMP and Ca; Naunyn-Schmiedebergs Arch Pharmacol 344; 682–690, 1992; Nielson C P et al., Effects of selective phosphodiesterase inhibitors on polymorphonuclear leucocyte respiratory burst. J Allergy Clin Immunol 86: 801–808, 1990; Schade et al., The specific type 3 and 4 phosphodiesterase inhibitor zardaverine suppresses formation of tumor necrosis factory by macrophages. European Journal of Pharmacology 230: 9–14, 1993).

Inhibition of PDE 4 Activity

Methodology

The activity test was carried out according to the method of Bauer and Schwabe, which was adapted to microtitre plates (Naunyn-Schmiederberg's Arch. Pharmacol. 311, 193–198, 1980). In this test, the PDE reaction is carried out in the first step. In a second step, the resultant 5'-nucleotide is cleaved to the uncharged nucleoside by a snake venom 5'-nucleotidase from Crotalus Atrox. In the third step, the nucleoside is separated from the remaining charged substrate on ion exchange columns. The columns are eluted directly into minivials using 2 ml of 30 mM ammonium formate (pH 6.0), to which a further 2 ml of scintillation fluid is added for counting.

For the following compounds inhibitory values [measured as $-\log IC_{50}$ (mol/l)] higher than 7.5 were determined. The numbers of the compounds correspond to the numbers of the examples.

Compound 10–33, 40, 41, 50, 52–55, 57, 59–64, 66–73, 75–892, 84, 86, 88–111, 115, 116, 118–121, 123–125

What is claimed is:

1. A compound of formula I

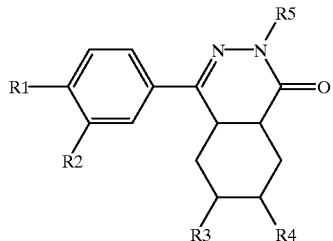

in which
R1 is 1-4C-alkoxy or 1-4C-alkoxy which is completely or predominantly substituted by fluorine,
R2 is 1-8C-alkoxy, 3-7C-cycloalkoxy, 3-7C-cycloalkylmethoxy or 1-4C-alkoxy which is completely or predominantly substituted by fluorine,
R3 and R4 are both hydrogen or together form an additional bond,
R5 is R6, —$C_mH_{2m}$—R7, —$C_nH_{2n}$—C(O)R8, —CH(R9)$_2$ —$C_pH_{2p}$—Ar, in which
  R6 is hydrogen (H), 1-8C-alkyl, 3-10C-cycloalkyl, 3-7C-cycloalkylmethyl, 3-7C-alkenyl, 3-7C-alkynyl, phenyl-3-4C-alkenyl, 7-10C-polycycloalkyl, naphthyl, pyridyl, pyrazinyl, pyridazinyl, pyrimidyl, quinazolinyl, quinoxalinyl, cinnolinyl, isoquinolyl, quinolyl, indanyl, benzoxazolyl, benzothiazolyl, oxazolyl, thiazolyl, N-methylpiperidyl, tetrahydropyranyl, tetrahydrothiapyranyl, or an unsubstituted or by R61 and/or R62 substituted phenyl radical, in which
    R61 is 1-4C-alkyl, 1-4C-alkoxy, nitro, halogen, carboxyl, carboxy-1-4C-alkyl, 1-4C-alkoxycarbonyl, hydroxy-1-4C-alkyl, amino, mono- or di-1-4C-alkylamino, 1-4C-alkylcarbonylamino, aminocarbonyl, mono- or di-1-4C-alkylaminocarbonyl, aminosulfonyl, mono- or di-1-4C-alkylaminosulfonyl, 4-methylphenylsulfonamido, tetrazol-5-yl, 2-(1-4C-alkyl)tetrazol-5-yl or 2-benzyl-tetrazol-5-yl and
    R62 is 1-4C-alkyl, 1-4C-alkoxy, nitro or halogen,
  R7 is hydroxyl, halogen, cyano, nitro, nitroxy(-O—NO$_2$), carboxyl, carboxyphenyloxy, phenoxy, 1-4C-alkoxy, 3-7C-cycloalkoxy, 3-7C-cycloalkylmethoxy, 1-4C-alkylcarbonyl, 1-4C-alkylcarbonyloxy, 1-4C-alkylcarbonylamino, 1-4C-alkoxycarbonyl, aminocarbonyl, mono- or di-1-4C-alkylaminocarbonyl, amino, mono- or di-1-4C-alkylamino, or an unsubstituted or by R71 and/or R72 substituted piperidyl, piperazinyl, pyrrolidinyl or morpholinyl radical, where
    R71 is hydroxyl, 1-4C-alkyl, hydroxy-1-4C-alkyl or 1-4C-alkoxycarbonyl, and
    R72 is 1-4C-alkyl, carboxyl, aminocarbonyl or 1-4C-alkoxycarbonyl,
  R8 is an unsubstituted or by R81 and/or R82 substituted phenyl, naphthyl, phenanthrenyl or anthracenyl radical, in which
    R81 is hydroxyl, halogen, cyano, 1-4C-alkyl, 1-4C-alkoxy, carboxyl, aminocarbonyl, mono- or di-1-4C-alkylaminocarbonyl, 1-4C-alkylcarbonyloxy, 1-4C-alkoxycarbonyl, amino, mono- or di-1-4C-alkylamino, 1-4C-alkylcarbonylamino, or 1-4C-alkoxy which is completely or predominantly substituted by fluorine, and
    R82 is hydroxyl, halogen, 1-4C-alkyl, 1-4C-alkoxy or 1-4C-alkoxy which is completely or predominantly substituted by fluorine,
  R9 is —$C_qH_{2q}$-phenyl,
  Ar is an unsubstituted phenyl, naphthyl, pyridyl, pyrazinyl, pyridazinyl, pyrimidinyl, quinazolinyl, quinoxalinyl, cinnolinyl, isoquinolyl, quinolyl, benzimidazolyl, benzoxazolyl, benzothiazolyl, benzotriazolyl, N-benzosuccinimidyl, imidazolyl, pyrazolyl, oxazolyl, thiazolyl, furyl, thienyl, pyrrolyl, a 2-(1-4C-alkyl)-thiazol-4-yl radical, or a phenyl radical substituted by R10 and/or R11, in which
    R10 is hydroxyl, halogen, nitro, 1-4C-alkyl, trifluoromethyl, 1-4C-alkoxy, carboxyl, carboxy-4-4-C-alkyl, 1-4C-alkylcarbonyloxy, 1-4C-alkoxycarbonyl, amino, mono- or di-1-4C-alkylamino, 1-4-C-alkylcarbonylamino, aminocarbonyl or mono- or di-1-4C-alkylaminocarbonyl, and
    R11 is hydroxyl, halogen, nitro, 1-4C-alkyl or 1-4C-alkoxy,
  m is an integer from 1 to 8,
  n is an integer from 1 to 4,
  p is an integer from 1 to 6,
  q is an integer from 0 to 2,
or a salt thereof.

2. A compound of formula I according to claim 1, in which
R1 is 1-4C-alkoxy or 1-4C-alkoxy which is completely or predominantly substituted by fluorine,
R2 is 1-8C-alkoxy, 3-7C-cycloalkoxy, 3-7C-cycloalkylmethoxy or 1-4C-alkoxy which is completely or predominantly substituted by fluorine,
R3 and R4 are both hydrogen or together form an additional bond,
R5 is R6, —$C_mH_{2m}$—R7, —$C_nH_{2n}$—C(O)R8, —CH(R9)$_2$ —$C_pH_{2p}$—Ar, in which
  R6 is hydrogen (H), 1-8C-alkyl, 3-10C-cycloalkyl, 3-7C-cycloalkylmethyl, 3-7C-alkenyl, 3-7C-alkynyl, phenyl-3-4C-alkenyl, bornyl, norbornyl, adamantyl or an unsubstituted or by R61 and/or R62 substituted phenyl radical, in which
    R61 is 1-4-C-alkyl, 1-4C-alkoxy, nitro or halogen, and
    R62 is 1-4C-alkyl, nitro or halogen,
  R7 is hydroxyl, halogen, cyano, nitro, carboxyl, phenoxy, 1-4-alkoxy, 3-7C-cycloalkoxy, 3-7C-cycloalkylmethoxy, 1-4C-alkylcarbonyl, 1-4C-alkylcarbonyloxy, 1-4C-alkylcarbonylamino, 1-4C-alkoxycarbonyl, aminocarbonyl, mono- or di-1-4C-alkylaminocarbonyl, amino, mono- or di-1-4C-alkylamino, or an unsubstituted or by R71 and/or R72 substituted piperidyl, piperazinyl, pyrrolidinyl or morpholinyl radical, where
    R71 is hydroxyl, 1-4C-alkyl, 1-4C-hydroxyalkyl or 1-4C-alkoxycarbonyl, and
    R72 is 1-4C-alkyl, carboxyl, aminocarbonyl or 1-4C-alkoxycarbonyl,
  R8 is an unsubstituted or by R81 and/or R82 substituted phenyl, naphthyl, phenanthrenyl or anthracenyl radical, in which
    R81 is hydroxyl, halogen, cyano, 1-4C-alkyl, 1-4C-alkoxy, carboxyl, aminocarbonyl, mono- or di-1-

4C-alkylaminocarbonyl, 1-4C-alkylcarbonyloxy, 1-4C-alkoxycarbonyl, amino, mono- or di-1-4C-alkylamino, 1-4C-alkylcarbonylamino, or 1-4C-alkoxy which is completely or predominantly substituted by fluorine, and R82 is hydroxyl, halogen, 1-4C-alkyl, 1-4C-alkoxy or 1-4C-alkoxy which is completely or predominantly substituted by fluorine, R9 is —$C_qH_{2q}$-phenyl, Ar is an unsubstituted phenyl, naphthyl, pyridyl, pyrazinyl, pyridazinyl, pyrimidinyl, quinazolinyl, quinoxalinyl, cinnolinyl, isoquinolyl, quinolyl, benzimidazolyl, benzoxazolyl, benzothiazolyl, benzotriazolyl, imidazolyl, pyrazolyl, oxazolyl, thiazolyl, furyl, thienyl, pyrrolyl, a 2-(1-4C-alkyl)-thiazol-4-yl radical, or a phenyl radical substituted by R10 and/or R11, in which R10 is hydroxyl, halogen, nitro, 1-4C-alkyl, trifluoromethyl, 1-4C-alkoxy, carboxyl, carboxy-1-4C-alkyl, 1-4C-alkylcarbonyloxy, 1-4C-alkoxycarbonyl, amino, mono- or di-1-4C-alkylamino, 1-4C-alkylcarbonylamino, aminocarbonyl or mono- or di-1-4C-alkylaminocarbonyl, and R11 is hydroxyl, halogen, nitro, 1-4C-alkyl or 1-4C-alkoxy, m is an integer from 1 to 8,
n is an integer from 1 to 4,
p is an integer from 1 to 4,
q is an integer from 0 to 2,
or a salt thereof.

3. A compound of formula I according to claim 1, in which

R1 is 1-4C-alkoxy or 1-2C-alkoxy which is completely or predominantly substituted by fluorine, R2 is 1-4C-alkoxy, 3-7C-cycloalkoxy, 3-7C-cycloalkylmethoxy or 1-2C-alkoxy which is completely or predominantly substituted by fluorine, R3 and R4 are both hydrogen or together form an additional bond, R5 is R6, —$C_mH_{2m}$—R7, —$C_nH_{2n}$—C(O)R8, —CH(R9)$_2$ or —$C_pH_{2p}$—Ar, in which R6 is hydrogen, 1-8C-alkyl, 3-8C-cycloalkyl, 3-7C-cycloalkylmethyl, 3-7C-alkenyl, 3-7C-alkynyl, phenyl-3-4C-alkenyl, bornyl, norbornyl, adamantyl, naphthyl, pyridyl, quinoxalinyl, indanyl, benzothiazolyl, N-methylpiperidyl, tetrahydropyranyl, tetrahydrothiopyranyl, or an unsubstituted or by R61 and/or R62 substituted phenyl radical, in which R61 is 1-2C-alkyl, 1-2C-alkoxy, nitro, halogen, carboxyl, carboxy-1-4C-alkyl, 1-4C-alkoxycarbonyl, hydroxy-1-4C-alkyl, amino, mono- or di-1-4C-alkylamino, aminocarbonyl, aminosulfonyl, mono- or di-1-4C-alkylaminosulfonyl, 4-methylphenylsulfonamido, tetrazol-5-yl, 2-(1-4C-alkyl)tetrazol-5-yl or 2-benzyltetrazol-5-yl, and R62 is 1-2C-alkyl, 1-2C-alkoxy, nitro, or halogen, R7 is hydroxyl, halogen, carboxyl, nitroxy (—O—NO$_s$), phenoxy, carboxyphenyloxy, 1-4C-alkoxy, 1-4C-alkylcarbonyl, 1-4C-alkylcarbonyloxy, 1-4C-alkylcarbonylamino, 1-4C-alkoxycarbonyl, aminocarbonyl, mono- or di-1-4-C-alkylaminocarbonyl, amino, mono- or di-1-4C-alkylamino, or an unsubstituted or by R71 and/or R72 substituted piperidyl, piperazinyl or morpholinyl radical, where R71 is hydroxyl, 1-4C-alkyl, 1-4C-hydroxyalkyl or 1-4C-alkoxycarbonyl, and R72 is 1-4-alkyl, carboxyl, aminocarbonyl or 1-4C-alkoxycarbonyl, R8 is an unsubstituted or by R81 and/or R82 substituted phenyl or naphthyl radical, where R8 1is hydroxyl, halogen, 1-4C-alkyl, 1-4C-alkoxy, 1-4C-alkylcarbonyloxy, 1-4C-alkylcarbonylamino, or 1-2C-alkoxy which is completely or predominantly substituted by fluorine, and R82 is halogen, 1-4C-alkyl or 1-4C-alkoxy, R9 is —$C_qH_{2q}$-phenyl, Ar is an unsubstituted phenyl, naphthyl, pyridyl, benzimidazolyl, benzoxazolyl, benzothiazolyl, benzotriazolyl, N-benzosuccinimidyl, imidazolyl, oxazolyl, thiazolyl, a 2-(1-2C-alkyl)-thiazol-4-yl radical, or a phenyl radical substituted by R10 and/or R11, in which R10 is hydroxyl, halogen, 1-4C-alkyl, trifluoromethyl, 1-4C-alkoxy, carboxyl, carboxy-1-4C-alkyl, 1-4C-alkylcarbonyloxy, 1-4C-alkoxycarbonyl and R11 is hydroxyl, halogen, 1-4C-alkyl or 1-4C-alkoxy, m is an integer from 1 to 8,
n is an integer from 1 to 4,
p is an integer from 1 to 6,
q is an integer from 0 to 1,
or a salt thereof.

4. A compound of formula I according to claim 1 in which

R1 is methoxy, ethoxy or difluoromethoxy,

R2 is 1-4C-alkoxy, difluoromethoxy, 3-5C-cycloalkoxy or 3-5C-cycloalkylmethoxy,

R3 and R4 are both hydrogen or together form an additional bond,

R5 is R4, —$C_mH_{2m}$—R7, —$C_nH_{2n}$—C(O)R8, —CH(R9)$_2$ or —$C_pH_{2p}$—Ar, in which R6 is hydrogen, 1-8C-alkyl, 3-8C-cycloalkyl, 3-7C-cycloalkylmethyl, 3-4C-alkenyl, 3-4C-alkynyl, phenyl-3-4C-alkenyl, adamantyl, pyridyl, quinoxalinyl, indanyl, benzothiazolyl, N-methylpiperidyl, tetrahydropyranyl, tetrahydrothiopyranyl, or an unsubstituted or by R61 and/or R62 substituted phenyl radical, in which R61 is 1-2C-alkyl, 1-2C-alkoxy, nitro, halogen, carboxyl, carboxy-1-2C-alkyl, 1-4C-alkoxycarbonyl, hydroxy-1-2C-alkyl, amino, aminosulfonyl, 4-methylphenylsulfonamido, 2-(1-2C-alkyl)tetrazol-5-yl or 2-benzyltetrazol-5-yl, and R62 is 1-2C-alkyl or halogen, R7 is hydroxyl, halogen, carboxyl, nitroxy (—O—NO$_2$), phenoxy, carboxyphenyloxy, 1-4C-alkoxycarbonyl, aminocarbonyl, mono- or di-1-4C-alkylaminocarbonyl, amino, mono- or di-1-4C-alkylamino, or an unsubstituted or by R71 and/or R72 substituted piperidyl, piperazinyl or morpholinyl radical, where R71 is hydroxyl, 1-4C-alkyl, 1-4C-hydroxyalkyl or 1-4C-alkoxycarbonyl, and R72 is 1-4C-alkyl, carboxyl, aminocarbonyl or 1-4C-alkoxycarbonyl, R8 is an unsubstituted or by R81 substituted phenyl or naphthyl radical where R81 is halogen or 1-4C-alkoxy, R9 is —C$_q$H$_{2q}$-phenyl, Ar is an unsubstituted phenyl, naphthyl, pyridyl, benzimidazolyl, benzotriazolyl, N-benzosuccinimidyl, imidazolyl, thiazolyl, a 2-(1-2C-alkyl)-thiazol-4-yl-radical, or a phenyl radical substituted by R10 and/or R11, in which R10 is hydroxyl, halogen, 1-2C-alkyl, trifluoromethyl, 1-2C-alkoxy, carboxyl, carboxy-1-2C-alkyl or 1-2C-alkoxycarbonyl, and R11 is halogen, 1-2C-alkyl or 1-2C-alkoxy, m is an integer from 1 to 8, n is an integer from 1 to 6, p is 1 or 2, q is 0 or 1, or a salt thereof.

5. A compound of formula I according to claim 1, in which

R1 is methoxy or ethoxy,

R2 is methoxy, ethoxy, difluoromethoxy, cyclopropylmethoxy or cyclopentyloxy,

R3 and R4 are both hydrogen or together form an additional bond,

R5 is R6, —C$_m$H$_{2m}$—R7, —C$_n$H$_{2n}$—C(O)R8, —CH(R9)$_2$ or —C$_p$H$_{2p}$—Ar, in which R6 is hydrogen, 1-8C-alkyl, 3-8C-cycloalkyl, 3-7C-cycloalkylmethyl, allyl, 2-propinyl, phenyl-trans-prop-1-en-3-yl, adamantyl, pyridyl, quinoxalinyl, indanyl, benzothiazolyl, N-methylpiperidyl, tetrahydropyranyl, tetrahydrothiopyranyl, or an unsubstituted or by R61 substituted phenyl radical, in which R61 is 1-4C-alkyl, nitro, halogen, carboxyl, carboxymethyl, hydroxy-1-2C-alkyl, amino, aminosulfonyl, 4-methylphenylsulfonamido, 2-ethyltetrazol-5-yl or 2-benzyltetrazol-5-yl, R7 is hydroxyl, halogen, carboxyl, nitroxy (—O—NO$_2$), phenoxy, carboxyphenyloxy, 1-4C-alkoxycarbonyl, amino, methylamino, dimethylamino, dimethylaminocarbonyl, 1-piperidyl or N-methyl-4-piperidyl, R8 is phenyl, 2-methoxyphenyl, 4-chlorophenyl or 2-naphthyl, R9 is —C$_q$H$_{2q}$-phenyl, Ar is an unsubstituted phenyl, pyridyl, benzimidazolyl, benzotriazolyl, N-benzosuccinimidyl, imidazolyl, a 2-methyl-thiazol-4-yl radical, or a phenyl radical substitued by R10 and/or R11, in which R10 is hydroxyl, halogen, methoxy, trifluoromethyl, carboxyl, carboxymethyl or methoxycarbonyl, and R11 is methoxy, m is an integer from 1 to 8, n is 1, p is an integer from 1 to 6, q is 0, or a salt thereof.

6. Compounds of the formula I according to claim 1, in which

R1 is methoxy,

R2 is methoxy, ethoxy, difluoromethoxy, cyclopropylmethoxy or cyclopentyloxy,

R3 and R4 are both hydrogen or together form an additional bond,

R5 is R6, —C$_n$H$_{2n}$—C(O)R8 or —C$_p$H$_{2p}$—Ar, in which

R6 is 3-8C-alkyl, 5-8C-cycloalkyl, 3-7C-cycloalkylmethyl, adamantyl, quinoxalinyl, indanyl, benzothiazolyl, tetrahydropyranyl, tetrahydrothiopyranyl, or an unsubstituted or by R61 substituted phenyl radical, in which R61 is 1-4C-alkyl, nitro, halogen, carboxyl, carboxymethyl, hydroxy-1-2C-alkyl, aminosulfonyl, 4-methylphenylsulfonamido, 2-ethyltetrazol-5-yl or 2-benzyltetrazol-5-yl, R8 is phenyl or 2-naphthyl, Ar is an unsubstituted phenyl, benzimidazolyl, N-benzosuccinimidyl, imidazolyl, or a phenyl radical substituted by R10, in which R10 is hydroxyl, halogen, methoxy, trifluoromethyl or carboxyl, n is 1, p is an integer from 1 to 6, or a salt thereof.

7. A compound of formula I according to claim 1, in which

R1 is methoxy or ethoxy,

R2 is methoxy, ethoxy or cyclopentyloxy,

R3 and R4 are both hydrogen or together form an additional bond,

R5 is R6, —C$_m$H$_{2m}$—R7, —C$_n$H$_{2n}$—C(O)R8, —CH(R9)$_2$ or —C$_p$H$_{2p}$—Ar, in which R6 is 1-6C-alkyl, 3-7C-cycloalkyl, 3-7C-cycloalkylmethyl, allyl, 2-propinyl, phenyl or phenyl-trans-prop-1-en-3-yl, R7 is hydroxyl, carboxyl or phenoxy, R8 is phenyl, 2-methoxyphenyl, 4-chlorophenyl or 2-naphthyl, R9 is —C$_q$H$_{2q}$-phenyl, Ar is an unsubstituted phenyl, pyridyl, benzotriazolyl, a 2-methyl-thiazol-4-yl radical, or a phenyl radical substituted by R10 and/or R11, in which R10 is hydroxyl, halogen, methoxy, trifluoromethyl, carboxyl, carboxymethyl or methoxycarbonyl, and R11 is methoxy, m is an integer from 1 to 6, n is 1, p is 1 or 2, q is 0, or a salt thereof.

8. A medicament composition which comprises an effective amount of a compound of claim 1 or a pharmaceutically-acceptable salt thereof together with a suitable pharmaceutical auxiliary or carrier.

9. A method for treating a subject afflicted with a condition amenable to treatment with a PDE inhibitor which comprises administering an effective amount of the PDE inhibitor to the subject and wherein the PDE inhibitor is a compound of claim 1 or a pharmaceutically-acceptable salt thereof.

10. A method of claim 9 wherein the condition is an airway disorder.

11. In a method for compounding a medicament composition, having an active ingredient for treating an airway disorder, by combining the active ingredient with a suitable pharmaceutical auxiliary or carrier, the improvement wherein said active ingredient is a compound of claim 1 or a pharmaceutically-acceptable salt thereof.

* * * * *